(12) United States Patent
Dann et al.

(10) Patent No.: US 7,794,447 B2
(45) Date of Patent: Sep. 14, 2010

(54) GASTROINTESTINAL SLEEVE DEVICE AND METHODS FOR TREATMENT OF MORBID OBESITY

(75) Inventors: Mitchell Dann, Wilson, WY (US); Lee Guterman, Amherst, NY (US)

(73) Assignee: ValenTx, Inc., Carpinteria, CA (US)

( * ) Notice: Subject to any disclaimer, the term of this patent is extended or adjusted under 35 U.S.C. 154(b) by 268 days.

(21) Appl. No.: 10/903,255

(22) Filed: Jul. 30, 2004

(65) Prior Publication Data
US 2005/0049718 A1   Mar. 3, 2005

Related U.S. Application Data

(63) Continuation of application No. 10/698,148, filed on Oct. 31, 2003.

(51) Int. Cl.
*A61M 31/00* (2006.01)
(52) U.S. Cl. .................... 604/516; 604/514
(58) Field of Classification Search ................ 604/264, 604/500–522; 623/23.65, 23.6; 606/153
See application file for complete search history.

(56) References Cited

U.S. PATENT DOCUMENTS

| | | | |
|---|---|---|---|
| 3,589,356 | A | 6/1971 | Silverman |
| 3,982,544 | A | 9/1976 | Dyck |
| 4,006,747 | A | 2/1977 | Kronenthal et al. |
| 4,043,345 | A | 8/1977 | Kramann et al. |
| 4,109,659 | A | 8/1978 | Sheridan |
| 4,134,405 | A | 1/1979 | Smit |
| 4,217,664 | A | 8/1980 | Faso |
| 4,235,238 | A | 11/1980 | Ogiu et al. |
| 4,252,131 | A | 2/1981 | Hon et al. |
| 4,271,839 | A | 6/1981 | Fogarty et al. |
| 4,315,509 | A | 2/1982 | Smit |
| 4,329,995 | A | 5/1982 | Anthracite |
| 4,501,264 | A * | 2/1985 | Rockey .............. 128/898 |
| 4,532,926 | A | 8/1985 | O'Holla |
| 4,606,347 | A | 8/1986 | Fogarty et al. |
| 4,641,653 | A | 2/1987 | Rockey |
| 4,719,916 | A * | 1/1988 | Ravo .............. 606/156 |

(Continued)

FOREIGN PATENT DOCUMENTS

EP    0817598    2/1996

(Continued)

OTHER PUBLICATIONS

*Endoscopic suturing*, C. Paul Swain MD, *Balliere's Clinical Gastroenterology*, vol. 13, No. 1. pp. 97-108, 1999.

(Continued)

*Primary Examiner*—Kevin C Sirmons
*Assistant Examiner*—Phillip Gray
(74) *Attorney, Agent, or Firm*—Knobbe, Martens, Olson & Bear, LLP

(57) ABSTRACT

Apparatus and methods are described for treatment of morbid obesity using minimally invasive techniques. The apparatus includes a system of components that may be used separately or in combination for effectively reducing stomach volume, bypassing a portion of the stomach and/or small intestines, reducing nutrient absorption in the stomach and/or small intestines and/or depositing minimally or undigested food farther than normal into the intestines, thereby stimulating intestinal responses. The components described include a gastric sleeve device, an intestinal sleeve device, and a combined gastrointestinal sleeve device.

10 Claims, 19 Drawing Sheets

U.S. PATENT DOCUMENTS

| | | |
|---|---|---|
| 4,763,653 A | 8/1988 | Rockey |
| 4,846,836 A | 7/1989 | Reich |
| 4,863,440 A | 9/1989 | Chin |
| 4,905,693 A * | 3/1990 | Ravo ............................ 606/153 |
| 4,946,440 A | 8/1990 | Hall |
| 5,085,661 A | 2/1992 | Moss |
| RE34,021 E | 8/1992 | Mueller et al. |
| 5,236,423 A | 8/1993 | Mix et al. |
| 5,306,300 A * | 4/1994 | Berry ........................ 623/23.64 |
| 5,314,473 A | 5/1994 | Godin |
| 5,318,530 A * | 6/1994 | Nelson, Jr. ................ 604/103.1 |
| 5,411,508 A | 5/1995 | Bessler et al. |
| 5,431,666 A | 7/1995 | Sauer et al. |
| 5,458,573 A | 10/1995 | Summers |
| 5,470,337 A | 11/1995 | Moss |
| 5,582,616 A | 12/1996 | Bolduc et al. |
| 5,645,568 A | 7/1997 | Chervitz et al. |
| 5,785,684 A | 7/1998 | Zimmon |
| 5,820,584 A | 10/1998 | Crabb |
| 5,824,008 A | 10/1998 | Bolduc et al. |
| 5,843,164 A | 12/1998 | Frantzen et al. |
| 5,861,036 A | 1/1999 | Godin |
| 5,887,594 A | 3/1999 | LoCicero, III |
| 5,957,940 A | 9/1999 | Tanner et al. |
| 5,972,023 A | 10/1999 | Tanner et al. |
| 5,997,556 A | 12/1999 | Tanner |
| 6,113,609 A | 9/2000 | Adams |
| 6,193,733 B1 | 2/2001 | Adams |
| 6,254,642 B1 | 7/2001 | Taylor |
| 6,264,700 B1 | 7/2001 | Kilcoyne et al. |
| 6,285,897 B1 | 9/2001 | Kilcoyne et al. |
| 6,312,437 B1 | 11/2001 | Kortenbach |
| 6,338,345 B1 | 1/2002 | Johnson et al. |
| 6,387,104 B1 | 5/2002 | Pugsley, Jr. et al. |
| 6,409,656 B1 | 6/2002 | Sangouard et al. |
| 6,447,533 B1 | 9/2002 | Adams |
| 6,494,888 B1 | 12/2002 | Laufer et al. |
| 6,520,974 B2 | 2/2003 | Tanner et al. |
| 6,535,764 B2 | 3/2003 | Imran et al. |
| 6,544,291 B2 | 4/2003 | Taylor |
| 6,558,400 B2 | 5/2003 | Deem et al. |
| 6,558,429 B2 | 5/2003 | Taylor |
| 6,592,596 B1 | 7/2003 | Geitz |
| 6,595,911 B2 | 7/2003 | LoVuolo |
| 6,626,916 B1 | 9/2003 | Yeung et al. |
| 6,626,919 B1 | 9/2003 | Swanstorm |
| 6,675,809 B2 | 1/2004 | Stack et al. |
| 6,699,263 B2 | 3/2004 | Cope |
| 6,702,735 B2 | 3/2004 | Kelly |
| 6,736,828 B1 | 5/2004 | Adams et al. |
| 6,740,121 B2 | 5/2004 | Geitz |
| 6,746,489 B2 | 6/2004 | Dua et al. |
| 6,764,518 B2 | 7/2004 | Godin |
| 6,773,452 B2 | 8/2004 | Shaker |
| 6,790,237 B2 | 9/2004 | Stinson |
| 6,845,776 B2 | 1/2005 | Stack et al. |
| 7,037,344 B2 | 5/2006 | Kagan et al. |
| 7,121,283 B2 | 10/2006 | Stack et al. |
| 7,146,984 B2 | 12/2006 | Stack et al. |
| 7,175,669 B2 | 2/2007 | Geitz |
| RE39,533 E | 3/2007 | Ranoux |
| 7,220,284 B2 | 5/2007 | Kagan et al. |
| 7,244,270 B2 | 7/2007 | Lesh |
| 7,267,694 B2 | 9/2007 | Levine et al. |
| 7,306,614 B2 | 12/2007 | Weller et al. |
| 7,309,341 B2 | 12/2007 | Ortiz et al. |
| 7,314,489 B2 | 1/2008 | McKenna et al. |
| 7,329,285 B2 | 2/2008 | Levine et al. |
| 7,347,875 B2 | 3/2008 | Levine et al. |
| 7,354,454 B2 | 4/2008 | Stack et al. |
| 2001/0016748 A1 | 8/2001 | Tanner et al. |
| 2001/0020189 A1 | 9/2001 | Taylor |
| 2001/0020190 A1 | 9/2001 | Taylor |
| 2001/0044595 A1 | 11/2001 | Reydel et al. |
| 2001/0056282 A1 | 12/2001 | Sonnenschein et al. |
| 2002/0016607 A1 | 2/2002 | Bonadio et al. |
| 2002/0026214 A1 | 2/2002 | Tanner et al. |
| 2002/0035370 A1 | 3/2002 | Kortenbach |
| 2002/0040226 A1 | 4/2002 | Laufer et al. |
| 2002/0058960 A1 | 5/2002 | Hudson et al. |
| 2002/0082621 A1 | 6/2002 | Schurr et al. |
| 2002/0165589 A1 | 11/2002 | Imaran et al. |
| 2002/0183768 A1 | 12/2002 | Deem et al. |
| 2002/0188354 A1 | 12/2002 | Peghini |
| 2003/0014064 A1 | 1/2003 | Blatter |
| 2003/0018358 A1 | 1/2003 | Saadat |
| 2003/0040804 A1 | 2/2003 | Stack et al. |
| 2003/0040808 A1 | 2/2003 | Stack et al. |
| 2003/0055313 A1 | 3/2003 | Anderson et al. |
| 2003/0055442 A1 | 3/2003 | Laufer et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0120285 A1 | 6/2003 | Kortenbach |
| 2003/0130560 A1 | 7/2003 | Suzuki et al. |
| 2003/0130561 A1 | 7/2003 | Suzuki et al. |
| 2003/0139752 A1 | 7/2003 | Pasricha et al. |
| 2003/0171775 A1 | 9/2003 | Belson |
| 2003/0181929 A1 | 9/2003 | Geitz |
| 2003/0191497 A1 | 10/2003 | Cope |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2004/0002734 A1 | 1/2004 | Fallin et al. |
| 2004/0024427 A1 | 2/2004 | Imran et al. |
| 2004/0039452 A1 * | 2/2004 | Bessler .................... 623/23.65 |
| 2004/0044364 A1 | 3/2004 | DeVries et al. |
| 2004/0059349 A1 | 3/2004 | Sixto, Jr. et al. |
| 2004/0059354 A1 | 3/2004 | Smith |
| 2004/0082963 A1 * | 4/2004 | Gannoe et al. .............. 606/153 |
| 2004/0087976 A1 | 5/2004 | DeVries et al. |
| 2004/0087977 A1 | 5/2004 | Nolan et al. |
| 2004/0088023 A1 | 5/2004 | Imran et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0093065 A1 | 5/2004 | Yachia et al. |
| 2004/0097986 A1 | 5/2004 | Adams |
| 2004/0097987 A1 | 5/2004 | Pugsley et al. |
| 2004/0102855 A1 | 5/2004 | Shank |
| 2004/0107004 A1 | 6/2004 | Levine et al. |
| 2004/0116949 A1 | 6/2004 | Ewers et al. |
| 2004/0117031 A1 | 6/2004 | Stack et al. |
| 2004/0122456 A1 | 6/2004 | Saadat et al. |
| 2004/0122473 A1 | 6/2004 | Ewers et al. |
| 2004/0133089 A1 | 7/2004 | Kilcoyne et al. |
| 2004/0133147 A1 | 7/2004 | Woo |
| 2004/0133219 A1 | 7/2004 | Forsell |
| 2004/0133238 A1 | 7/2004 | Cerier |
| 2004/0138525 A1 | 7/2004 | Saadat et al. |
| 2004/0138529 A1 | 7/2004 | Wiltshire et al. |
| 2004/0138761 A1 | 7/2004 | Stack et al. |
| 2004/0143342 A1 | 7/2004 | Stack et al. |
| 2004/0147958 A1 | 7/2004 | Lam et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162567 A9 | 8/2004 | Adams |
| 2004/0162568 A1 | 8/2004 | Saadat et al. |
| 2004/0167546 A1 | 8/2004 | Saadat et al. |
| 2004/0181242 A1 | 9/2004 | Stack et al. |

| | | |
|---|---|---|
| 2004/0186514 A1 | 9/2004 | Swain et al. |
| 2004/0193190 A1 | 9/2004 | Liddicoat et al. |
| 2004/0204768 A1 | 10/2004 | Geitz |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0243195 A1 | 12/2004 | Imran et al. |
| 2004/0249362 A1 | 12/2004 | Levine et al. |
| 2004/0249367 A1 | 12/2004 | Saadat et al. |
| 2005/0033240 A1 | 2/2005 | Oishi et al. |
| 2005/0033331 A1 | 2/2005 | Burnett et al. |
| 2005/0033332 A1 | 2/2005 | Burnett et al. |
| 2005/0049718 A1 | 3/2005 | Dann |
| 2005/0065401 A1 | 3/2005 | Saadat |
| 2005/0075654 A1 | 4/2005 | Kelleher |
| 2005/0080431 A1 | 4/2005 | Levine et al. |
| 2005/0080444 A1 | 4/2005 | Kraemer et al. |
| 2005/0085787 A1 | 4/2005 | Laufer |
| 2005/0085900 A1 | 4/2005 | Case et al. |
| 2005/0085923 A1 | 4/2005 | Levine et al. |
| 2005/0096673 A1 | 5/2005 | Stack et al. |
| 2005/0096750 A1 | 5/2005 | Kagan |
| 2005/0101977 A1 | 5/2005 | Gannoe |
| 2005/0125020 A1 | 6/2005 | Meade et al. |
| 2005/0125075 A1 | 6/2005 | Meade et al. |
| 2005/0143784 A1 | 6/2005 | Imran |
| 2005/0177181 A1 | 8/2005 | Kagan |
| 2005/0187567 A1 | 8/2005 | Baker et al. |
| 2005/0192629 A1 | 9/2005 | Jaadat et al. |
| 2005/0197714 A1 | 9/2005 | Sayet |
| 2005/0197715 A1 | 9/2005 | Kugler et al. |
| 2005/0203547 A1 | 9/2005 | Weller et al. |
| 2005/0247320 A1 | 11/2005 | Stack et al. |
| 2005/0256587 A1 | 11/2005 | Egan |
| 2005/0261549 A1 | 11/2005 | Hewit et al. |
| 2005/0261712 A1 | 11/2005 | Balbierz et al. |
| 2005/0267499 A1 | 12/2005 | Stack et al. |
| 2006/0009858 A1 | 1/2006 | Levine et al. |
| 2006/0015125 A1 | 1/2006 | Swain |
| 2006/0020164 A1 | 1/2006 | Butler et al. |
| 2006/0020247 A1 | 1/2006 | Kagan |
| 2006/0020254 A1 | 1/2006 | von Hoffmann |
| 2006/0020277 A1 | 1/2006 | Gostout et al. |
| 2006/0020278 A1 | 1/2006 | Burnett et al. |
| 2006/0025819 A1 | 2/2006 | Nobis et al. |
| 2006/0047289 A1 | 3/2006 | Fogel |
| 2006/0064120 A1 | 3/2006 | Levine et al. |
| 2006/0074458 A1 | 4/2006 | Imran |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0173422 A1 | 8/2006 | Reydel et al. |
| 2006/0206063 A1 | 9/2006 | Kagan |
| 2006/0206064 A1 | 9/2006 | Kagan |
| 2006/0235446 A1 | 10/2006 | Godin |
| 2006/0265082 A1 | 11/2006 | Meade et al. |
| 2006/0287734 A1 | 12/2006 | Stack et al. |
| 2006/0293742 A1 | 12/2006 | Dann |
| 2007/0005147 A1 | 1/2007 | Levine et al. |
| 2007/0010794 A1 | 1/2007 | Dann |
| 2007/0010864 A1 | 1/2007 | Dann |
| 2007/0010865 A1 | 1/2007 | Dann |
| 2007/0010866 A1 | 1/2007 | Dann |
| 2007/0016244 A1 | 1/2007 | Behl et al. |
| 2007/0027548 A1 | 2/2007 | Levine et al. |
| 2007/0027549 A1 | 2/2007 | Godin |
| 2007/0032879 A1 | 2/2007 | Levine et al. |
| 2007/0083271 A1 | 4/2007 | Levine et al. |
| 2007/0106233 A1 | 5/2007 | Huang et al. |
| 2007/0129719 A1 | 6/2007 | Kendale et al. |
| 2007/0208360 A1 | 9/2007 | Demarais et al. |
| 2007/0225555 A1 | 9/2007 | Stefanchik |
| 2007/0233162 A1 | 10/2007 | Gannoe et al. |
| 2007/0293885 A1 | 12/2007 | Binmoeller |
| 2008/0004606 A1 | 1/2008 | Swain et al. |
| 2008/0058887 A1 | 3/2008 | Griffin et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2009/0012356 A1 | 1/2009 | Dann et al. |
| 2009/0012541 A1 | 1/2009 | Dahl et al. |
| 2009/0012544 A1 | 1/2009 | Thompson et al. |
| 2009/0012553 A1 | 1/2009 | Swain et al. |

FOREIGN PATENT DOCUMENTS

| | | |
|---|---|---|
| WO | WO 80/00007 | 1/1980 |
| WO | WO 98/56440 A1 | 12/1998 |
| WO | WO 01/43663 | 6/2001 |
| WO | WO 03/017882 A2 | 3/2003 |
| WO | WO 03/086247 A1 | 10/2003 |
| WO | WO 03/094785 A1 | 11/2003 |
| WO | WO 2004/017863 A2 | 3/2004 |
| WO | WO 2004/047686 | 6/2004 |
| WO | WO 2004/049982 A2 | 6/2004 |
| WO | WO 2004/064680 A1 | 8/2004 |
| WO | WO 2004/080336 A2 | 9/2004 |
| WO | WO 2004/086984 A1 | 11/2004 |
| WO | WO 2004/105643 | 12/2004 |
| WO | WO 2005/011519 | 2/2005 |
| WO | WO 2005/032422 | 4/2005 |
| WO | WO 2005/037152 A1 | 4/2005 |
| WO | WO 2005/060869 A1 | 7/2005 |
| WO | WO 2005/060882 A1 | 7/2005 |

OTHER PUBLICATIONS

Endoscopic Suturing of a Novel Gastroesophageal Antireflux Device (GARD) A Prelinary Report, N.J. Godin et al., *Gastrointestinal Endoscopy*, vol. 43, No. 4, 1996.

An endoscopic stapling device: the development of new flexible endoscopically controlled device for placing multiple transmural staples in gastrointestinal tissue, C. Paul Swain, MD et al., *Gastrointestinal Endoscopy*, vol. 35, No. 4, 1989 pp. 338-339.

An endoscopically deliverable tissue-transfixing device for securing biosensors in the gastrointestinal tract, C. Paul Swain, MD et al. *Gastrointestinal Endoscopy*, 1994 vol. 40 No. 6 pp. 730-734.

*Development of a gastroplasty with variable diameter. Experimental study using artificial sphincters*, M. Merlini et al., 1992 Abstract.

A through-the-scope device of suturing and tissue approximation under EUS control, Annette Fritscher-Ravens, MD, et al., *Gastrointestinal Endoscopy*, vol. 56, No. 5, 2002, pp. 737-742.

Bard EndoCinch: the device, the technique and pre-clinical studies, Paul Swain, M.D. et al., *Gastrointestinal Endoscopy Clinics of North America*, 13, 2003 pp. 75-88.

Microvasive gastric stapler: the device, technique, and preclinical results, Tom R. De Meester MD, *Gastrointestinal Endoscopy Clinics of North America*, 13 (2003) pp. 117-133.

Transgastric gastropexy and hiatal hernia repair for GERD under EUS control: a porcine model, Annette Fritscher-Ravens, MD et al., *Gastrointestinal Endoscopy*, vol. 59, No. 1, 2004, pp. 89-95.

*T=Anchor Introducer Gun™ Details*, Moss™ Tubes Brochure.

Sew-Right® SR 5™ & SR 10™, Ti-KNOT® TK 5™ Advertisement received at ASBS Conference 2002.

PCT International Search Report, PCT/US2003/34822 mailed Feb. 4, 2004.

PCT International Search Report, PCT/US2004/44049 mailed May 30, 2007.

PCT International Search Report for PCT/US07/08882, mailed Dec. 26, 2007.

Fobi, M.D., Mathais A.L. et al., "Gastric Bypass Operation for Obesity", World J. Surg., Sep. 1998, vol. 22, pp. 925-935.

Pories, M.D., Walter J. et al., "Who Would Have Thought It? An Operation Proves to Be the Most Effective Therapy for Adult-Onset Diabetes Mellitus", Annals of Surgery, Sep. 1995, vol. 222, No. 3, pp. 339-352.

Sugerman, M.D., Harvey J. et al., "Weight Loss With Vertical Banded Gastroplasty and Roux-Y Gastric Bypass for Morbid Obesity With Selective Versus Random Assignment", The American Journal of Surgery, Jan. 1989, vol. 157, pp. 93-102.

Keyser, M.D., Eric J. et al., "Double Closed Loop Obstruction and Perforation in a Previous Roux-en-Y Gastric Bypass", Obesity Surgery, 1998, vol. 8, pp. 475-479.

Oh, M.D., Chung H. et al., "Weight Loss Following Transected Gastric Bypass with Proximal Roux-en-Y", Obesity Surgery, 1997, vol. 7, pp. 142-147.

Crampton, MBBS, Nicholas A., et al., "Silastic Ring Gastric Bypass: Results in 64 Patients", Obesity Surgery, 1997, vol. 7, pp. 489-493.

Yamamoto et al. "A new method of enteroscopy—The double-balloon method", Can J. Gastroenterol, vol. 17, No. 4 Apr. 2003, pp. 273-274.

Swain et al., "Radiocontrolled Movement of a Robot Endoscope in the Human Gastrointestinal Tract", Abstract—Gastrointestinal Endoscopy, vol. 61, No. 5 DDW Abstract Issue: Apr. 2005.

Long et al. "Techniques for Advancing Guide Wires and Devices in the Lumen of the Gastrointestinal Tract", Gastrointestinal Endoscopy, vol. 57, No. 5 Apr. 2003 Abstract, 2003 ASGE Meeting, May 18-21, Orlando Florida.

U.S. Appl. No. 11/431,040, filed May 2006, Kagan.

U.S. Appl. No. 11/548,605, filed Oct. 2006, Dann.

\* cited by examiner

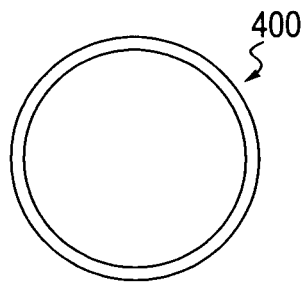
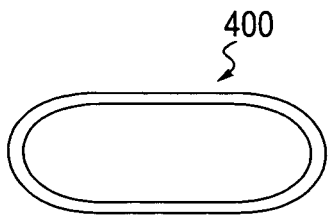
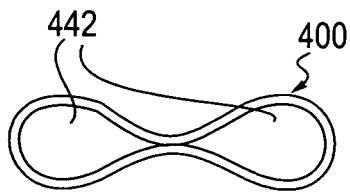
FIG 12A  FIG 12B  FIG 12C
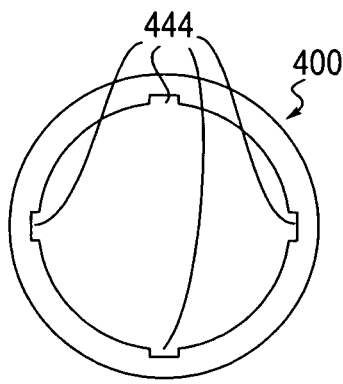
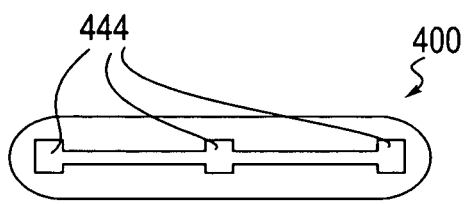
FIG 13A  FIG 13B
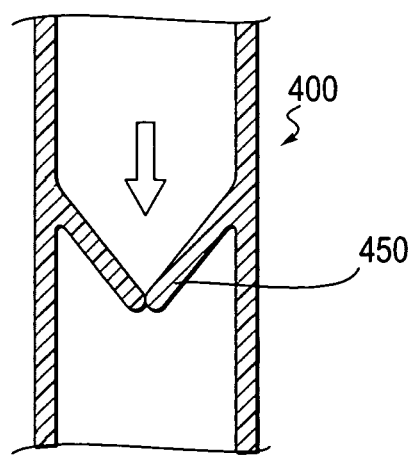
FIG 14

GASTROINTESTINAL SLEEVE DEVICE AND METHODS FOR TREATMENT OF MORBID OBESITY

CROSS-REFERENCE TO OTHER APPLICATIONS

The present application is a continuation of U.S. patent application Ser. No. 10/698,148, filed on Oct. 31, 2003, for Apparatus and Methods for Treatment of Morbid Obesity, which claims priority of U.S. Provisional Patent Applications 60/442,987, filed on Nov. 1, 2002, for Apparatus and Methods for Treatment of Morbid Obesity; 60/430,857, filed on Dec. 3, 2002, for Biliopancreatic Diverter Tube for Treatment of Morbid Obesity; 60/437,513, filed on Dec. 30, 2002, for Apparatus and Methods for Gastric Surgery, 60/448,817, filed on Feb. 21, 2003, for Surgical Fastener System and Method for Attachment within a Hollow Organ, and 60/480,485, filed on Jun. 21, 2003 for Gastrointestinal Sleeve Device and Method of Use. These and all other patents and patent applications referred to herein are hereby incorporated by reference in their entirety.

FIELD OF THE INVENTION

The present invention relates generally to apparatus and methods for treatment of obesity, and particularly morbid obesity. In particular, it relates to apparatus and methods that can be applied using minimally invasive techniques for effectively reducing stomach volume, bypassing a portion of the stomach and/or small intestines and/or reducing nutrient absorption in the stomach and/or small intestines.

BACKGROUND OF THE INVENTION

Bariatrics is the field of medicine encompassing the study of overweight, its causes, prevention and treatment. Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty. A more complete history of bariatric surgery can be found in U.S. Provisional Patent Application No. 60/422,987 Apparatus and Methods for Treatment of Morbid Obesity and also on the website of the American Society for Bariatric Surgery at http://www.asbs.org.

Medical sleeve devices for placement in a patient's stomach are described by Rockey in U.S. Pat. Nos. 4,501,264, 4,641,653 and 4,763,653. The medical sleeve described in these patents are said to reduce the surface area available for absorption in the stomach, however it is not configured to effectively reduce the volume of the stomach nor will the device described isolate ingested food from stomach secretions. The medical sleeve is not configured to be deployed in a patient's small intestine.

Other sleeve devices for placement in a patient's intestines are described in U.S. Pat. No. 4,134,405 (Smit), U.S. Pat. No. 4,315,509 (Smit), U.S. Pat. No. 5,306,300 (Berry), and U.S. Pat. No. 5,820,584 (Crabb). The sleeve devices described in these patents are said to be placed at the lower end of the stomach and therefore do not serve to isolate ingested food from the digestive secretions of the stomach. These sleeve devices are not configured to be deployed in a patient's stomach or to effectively reduce the volume of the patient's stomach or small intestine.

In U.S. patent application Ser. No. 2003/0040804, Stack et al. describe a satiation device to aid in weight loss by controlling feelings of hunger. The patent application describes an antral tube that expands into the antrum of the stomach to create a feeling of satiation. The devices described are not configured to isolate ingested food and liquids from digestive secretions in the stomach or the intestines.

In U.S. patent application Ser. No. 2003/0040808, Stack et al. describe a satiation device for inducing weight loss in a patient includes a tubular prosthesis positionable at the gastro-esophageal junction region, preferably below the z-line. The prosthesis is placed such that an opening at its proximal end receives masticated food from the esophagus, and such that the masticated food passes through the pouch and into the stomach via an opening in its distal end.

In U.S. patent application Ser. No. 2003/0093117, Sadaat describes an implantable artificial partition that includes a plurality of anchors adapted for intraluminal penetration into a wall of the gastro-intestinal lumen to prevent migration or dislodgement of the apparatus, and a partition, which may include a drawstring or a toroidal balloon, coupled to the plurality of anchors to provide a local reduction in the cross-sectional area of the gastro-intestinal lumen.

In U.S. patent application Ser. No. 2003/0120265, Deem et al. describe various obesity treatment tools and methods for reducing the size of the stomach pouch to limit the caloric intake as well as to provide an earlier feeling of satiety. The smaller pouches may be made using individual anchoring devices, rotating probes, or volume reduction devices applied directly from the interior of the stomach. A pyloroplasty procedure to render the pyloric sphincter incompetent and a gastric bypass procedure using atraumatic magnetic anastomosis devices are also described.

In U.S. patent application Ser. No. 2003/0144708, Starkebaum describes methods and systems for treating patients suffering from eating disorders and obesity using electrical stimulation directly or indirectly to the pylorus of a patient to substantially close the pylorus lumen to inhibit emptying of the stomach.

SUMMARY OF THE INVENTION

In keeping with the foregoing discussion, the present invention provides apparatus and methods that can be applied using minimally invasive techniques for treatment of obesity, and particularly morbid obesity. The apparatus takes the form of a system of components that may be used separately or in combination for effectively reducing stomach volume, bypassing a portion of the stomach and/or small intestines, reducing nutrient absorption in the stomach and/or small intestines and/or depositing minimally or undigested food farther than normal into the intestines (thereby stimulating intestinal responses).

In one aspect of the invention, the system may include an artificial stoma device located in the stomach or lower esophagus that can reduce the flow of food into the stomach (when located in the stomach) or back from the stomach into the esophagus (when located in the esophagus or at the gastroesophageal junction). Alternatively, the system may utilize a surgically created artificial stoma. The stoma is introduced transesophageally and implanted under visualization with a flexible endoscope. The stoma may be anchored to the esophageal or stomach wall using sutures, staples or clips. Alternatively, the stoma may be anchored with a sutureless attachment that does not penetrate the esophageal or stomach wall. Optionally, the stoma may be used in conjunction with gastric suturing, stapling or banding to create a narrow passage for installation of the stoma and/or for reduction of gastric volume. The gastric stapling or banding may be applied using transesophageal or laparoscopic techniques.

In another aspect, the system may include an internal gastric sleeve that may be used separately or used with, attached to or integrated with the artificial stoma component. The gastric sleeve may have a funnel-shaped entry with a reinforced anchoring segment or other anchoring mechanism for attachment in the stomach at or near the gastroesophageal junction. Optionally, the artificial stoma component may be positioned a clinically significant distance distal to the sleeve attachment. When placed in the stomach, the entry portion of the sleeve proximate to the stoma effectively reduces the volume of the stomach because the flow of solid food is limited to the lumen of the sleeve. When combined with a restrictive stoma, the sleeve functions as the pouch in a gastric bypass or vertical banded (or other) gastroplasty. The sleeve can be designed and placed to maximize the amount of stomach wall included by the sleeve opening and therefore included in the pouch thereby formed. This will enable a maximum number of stretch receptors and other stimulating mechanisms in the stomach to transmit satiety (fullness) signals to help reduce food intake.

The entire gastric sleeve or a portion of it can be porous or semipermeable to allow the flow of digestive secretions into the sleeve and to allow the flow of nutrients and/or fluids out through the wall of the gastric sleeve. Valves may be provided in the wall of the gastric sleeve to allow digestive secretions to enter the sleeve, but to prevent solid food and/or nutrients from flowing out through the wall of the sleeve. Alternatively, the entire gastric sleeve or a portion of it can be nonporous or impermeable to act as an internal gastric bypass. In certain embodiments, the wall of the gastric sleeve is flexible to allow the peristaltic motions of the stomach to effect movement of food through the gastric sleeve. The wall of the sleeve may be reinforced with rings or a spiral made of wire and/or plastic. Alternatively, the gastric sleeve may be attached to an artificial stoma component that includes its own anchoring mechanism. Optionally, the distal end of the gastric sleeve may be anchored in the region of the pylorus. Optionally the distal end of the gastric sleeve can incorporate an enlarged reservoir portion proximal to the pylorus. Optionally the sleeve can include coatings on its interior and/or exterior to enhance the surface properties of the sleeve in clinically relevant manners.

In conjunction with the stoma and/or gastric sleeve, the volume of the stomach can be reduced by suturing, stapling using open, transesophageal or laparoscopic techniques. Alternatively or in addition, a gastric balloon or other volume displacement device may be used in conjunction with the gastric sleeve to provide a feeling of satiety. These adjunctive techniques have the effect of further reducing nutrient intake (in the case of a stomach reduction and pouch formation upstream of a stoma) and enhancing the effect of peristaltic motions of the stomach for moving food through the gastric sleeve intake (in the case of a stomach reduction downstream of a stoma where there is a gastric sleeve). A gastric sleeve that extends beyond the pylorus, with or without an intestinal sleeve, can allow use of the pylorus as a natural stoma by configuring the sleeve to close by the pylorus and then open to allow passage of food when the muscles of the pylorus relax.

One advantage of using an internal gastric sleeve over prior art gastric volume reduction techniques is that volume reduction can be better defined in that the patient cannot deliberately or inadvertently increase the volume of the sleeve over time by overeating as occurs when the stomach wall stretches. Another advantage of an internal sleeve over prior art banding techniques is that stomach wall is not trapped between an external structure and ingested food whereby the stomach wall is subject to compression due to overeating.

In another aspect, the system may include an internal intestinal sleeve that may be used separately or used with, attached to or integrated with the internal gastric sleeve and/or artificial stoma component. The entire intestinal sleeve or a portion of it can be porous or semipermeable to allow the flow of digestive secretions into the sleeve and to allow the flow of nutrients and/or fluids out through the wall of the sleeve. Valves may be provided in the wall of the intestinal sleeve to allow digestive secretions to enter the sleeve, but to prevent solid food and/or nutrients from flowing out through the wall of the sleeve. Alternatively, the entire intestinal sleeve or a portion of it can be nonporous or impermeable to act as an internal intestinal bypass. In certain embodiments, the wall of the intestinal sleeve is flexible to allow the peristaltic motions of the intestinal wall to effect movement of food through the intestinal sleeve. The wall of the sleeve may be reinforced with rings or a spiral made of wire and/or plastic. Optionally these components can include radiopaque materials for visualization of the device when it is in the body. Optionally the sleeve can include coatings on its interior and/or exterior to enhance the surface properties of the sleeve in clinically relevant manners.

In one aspect of the present invention, there is provided a method of treating a patient. The method includes the steps of providing a gastrointestinal sleeve having a proximal end, a distal end and a length of at least about 50 cm. The sleeve is positioned with the proximal end adjacent an attachment site in the vicinity of the lower esophageal sphincter, with the distal end extending transluminally at least as far as the jejunum. The distal end of the sleeve may extend into the intestine at least as far as the ligament of Treitz. The providing step may comprise providing a sleeve having a substantially constant diameter throughout its length.

Optionally, the intestinal sleeve may have a proximal end with a reinforced anchoring segment or other anchoring mechanism for attachment in the region of the pylorus. Alternatively, the intestinal sleeve may be attached to or continuous with the internal gastric sleeve. Optionally, the distal end of the intestinal sleeve may include an anchoring mechanism.

Optionally, the above system components can include means of separately installing, replacing and/or removing single components. This would include means of reversibly attaching and connecting components. This would allow a therapeutic device to be assembled over multiple operations or in a single procedure. Alternatively, the above components can be preassembled with a specific combination of desired features for an individual patient and thereby installed and removed in a single operation. Preferably, each component of the system includes one or more radiopaque and/or sonoreflective markers for enhanced imaging by X-ray, fluoroscopy and/or ultrasonic imaging.

Certain implementations of the invention will achieve some or all of the following advantages:

1. Minimally invasive, peroral/transesophageal implantation, with optional surgical and/or laparoscopic assist 2. Customizable to each patient and revisable in-situ based upon the results of the intervention 3. Completely reversible using minimally invasive techniques 4. Lower morbidity, mortality 5. When used with a gastric and/or intestinal sleeve, does not allow an appreciable amount of digestion to occur until the food exits the sleeve into the intestine by keeping food separate from gastric and/or intestinal secretions. This delivers undigested food to the jejunum where a dumping syndrome reaction and/or other results of overstimulation of the intestine may occur depending upon the clinical situation and the food ingested.

BRIEF DESCRIPTION OF THE DRAWINGS

FIGS. 12A, 12B and 12C show a cross section of the gastrointestinal sleeve device with optional features intended to keep the lumen of the sleeve open even if the sleeve collapses.

FIGS. 13A and 13B show a cross section of the gastrointestinal sleeve device with optional internal channels intended to keep the lumen of the sleeve open even if the sleeve collapses.

FIG. 14 illustrates an optional one-way valve feature of the gastrointestinal sleeve device.

DETAILED DESCRIPTION OF THE PREFERRED EMBODIMENT

The present invention provides apparatus and methods for treatment of obesity, and particularly morbid obesity. The apparatus takes the form of a system of components that may be used separately or in combination for effectively reducing stomach volume, bypassing a portion of the stomach and/or small intestines and reducing nutrient absorption in the stomach and/or small intestines. Each of the components can be implanted using minimally invasive techniques, preferably using a transesophageal approach under visualization with a flexible endoscope. Optionally, laparoscopic surgical techniques may be used to assist in the implantation of the components and/or for adjunctive therapies in the digestive tract.

In the following, the word endoscope (and endoscopic) will refer to an instrument for visually examining the interior of a bodily canal or a hollow organ. For procedures performed via a peroral route, a flexible endoscope, such as a gastroscope, is generally preferred. The word laparoscope (laparoscopic) will refer to rigid endoscopes generally passed through surgically created portals. Also in the following the terms biodegradable and bioresorbable will be used interchangeably. Also in the following the term stoma will be used to refer to an opening formed in a hollow organ which may or may not be configured to restrict flow of food and/or digestive juices. Endoscopic overtube and orogastric tube sleeve are also used interchangeably.

Figure 1:
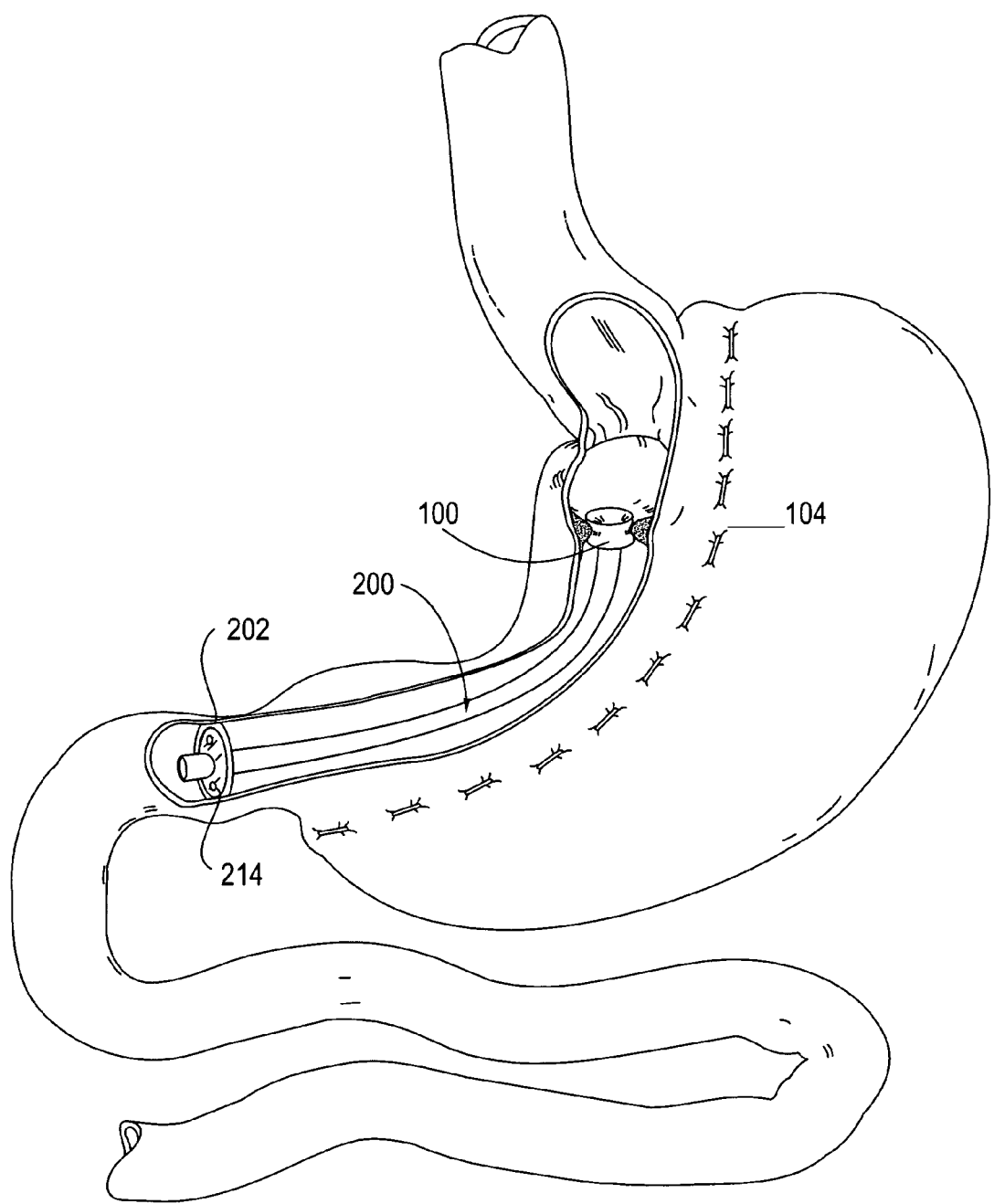
FIG. 1 shows a gastric sleeve device with an artificial stoma device and a pyloric sleeve anchor implanted within a patient's stomach with a line of gastroplasty sutures or staples parallel to the sleeve.

In one aspect of the invention, the system may include an artificial stoma 100 located in the stomach or lower esophagus that can optionally reduce the flow of food into the stomach. FIG. 1 shows an artificial stoma device 100 implanted within a patient's stomach. The stoma device 100 is introduced transesophageally and implanted under visualization with a flexible endoscope. The stoma may be optionally restrictive or non-restrictive of food flow. The stoma may be anchored to the esophageal or stomach wall using sutures, staples, clips or other anchoring mechanisms as described herein. Optionally, the stoma 100 may be used in conjunction with gastric suturing, stapling or banding to create a narrow passage for installation of the stoma and/or for reduction of gastric volume. The gastric suturing, stapling or banding may be applied using open, transesophageal or laparoscopic techniques. The gastroplasty sutures or staples 104 may be applied using open, transesophageal or laparoscopic techniques.

The artificial stoma 100 may include a fabric cuff on the outer circumference to facilitate ingrowth of tissue to secure the stoma device 100 in place. In-growth can be further facilitated by partial transection of the gastric wall through the mucosa. This will put the fabric cuff in contact with muscularis. Alternatively or in addition, a number of suture attachment points can be included on the outer circumference of the stoma device. The suture attachment points may take the form of suture attachment loops attached to the outer circumference of the stoma device or a ring with suture attachment holes formed in it.

In certain embodiments, the outer circumference of the stoma 100 is flexible and elastic with properties to minimize the resistance of the stoma 100 to motion of the stomach at the stomal attachment points. This also serves to minimize the forces that can lead to tissue erosion.

Preferably, the stoma device is constructed with radiopaque and/or sonoreflective materials and/or includes one or more radiopaque and/or sonoreflective markers for enhanced imaging by X-ray, fluoroscopy and/or ultrasonic imaging so that the position and functional state of the implanted stoma device can be verified noninvasively in addition to endoscopic direct visualization. Additional details of the artificial stoma 100 construction can be found in U.S. patent application Ser. No. 10/698,148.

In another aspect, the system may include an internal gastric sleeve 200 that may be used separately or used with, attached to or integrated with the artificial stoma component 100. FIG. 1 shows a gastric sleeve device 200 with an artificial stoma device 100 implanted within a patient's stomach. Optionally the sleeve can be attached to the outlet of a surgically created stoma or pouch that does not include an artificial implanted stoma. The gastric sleeve device 200 may include a pyloric sleeve anchor 202 for anchoring the distal end of the sleeve 200 in the region of the pylorus. The pyloric sleeve anchor 202 can be configured with openings 214 to allow digestive secretions to pass through the pylorus into the small intestine. The internal gastric sleeve 200 effectively reduces the volume of the stomach because the flow of solid food is limited to the lumen of the sleeve 200. The entire gastric sleeve 200 or a portion of it can be porous or semipermeable to allow the flow of digestive secretions into the sleeve and to allow the flow of nutrients and/or fluids out through the wall of the gastric sleeve 200. Porosity can be achieved for example by forming holes in the sleeve using a laser or mechanical means. Semipermeable areas of the sleeve can be formed, for example, from silicone or materials used for hemodialysis membranes.

Pyloric anchors can be fixed to a predetermined location on the sleeve or be mobile. For example, a pyloric anchor could be slidable and slid into place before it is fixed to a structure on the sleeve. Structures for anchor fixation could include reinforcement and/or structures such as snaps, loops and/or holes to facilitate attachment of the anchor to the sleeve. Slidable or other structures that allow positioning of an anchor can be used to set the distance between the attachment of the sleeve near the GEJ and the support or strain relief provided by the anchor at the pylorus. This distance can be set prior to placement of the device, based upon fluoroscopic or other measurements or in vivo. If the distance is set in vivo, structure could be provided to allow fixation using commercially available tools such as ENDOCINCH (Bard), ENDOSCOPIC SUTURING DEVICE (Wilson-Cook Medical) or PLICATOR (NDO Surgical Inc.) or an endoscopic grasper. Alternately, a structure that requires a special attachment device, such as the riveters described herein could be used.

In some clinical situations it could be beneficial to have an anchor designed to allow motion. This could include some means to bias the anchor to return to a predetermined location relative to a set position on the sleeve. This could be accomplished by incorporation of a spring, elastomeric structure or other such biasing structure.

Figure 2A:
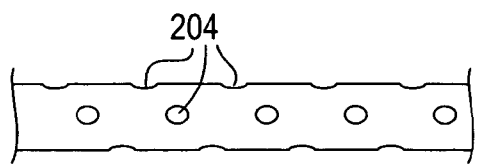
FIGS. 2A-2E are detail drawings showing additional features of a gastric or intestinal sleeve device.
Figure 2B:
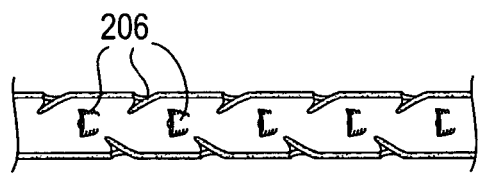
Figure 2C:
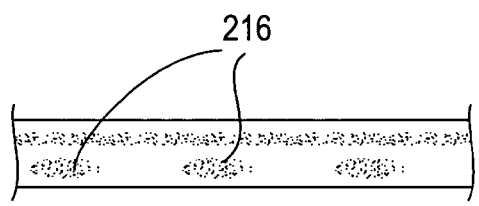
Figure 2D:
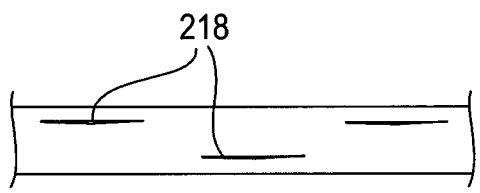
Figure 2E:
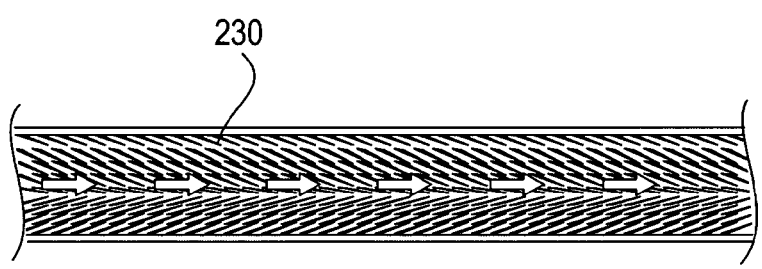

FIGS. 2A-2E are detail drawings showing additional features of a gastric or intestinal sleeve device. FIG. 2A shows a detail drawing of a gastric and/or intestinal sleeve device with openings 204 through the sleeve wall. Valves 206 may be provided in the wall of the gastric sleeve to allow digestive secretions to enter the sleeve, but to prevent solid food and/or nutrients from flowing out through the wall of the sleeve. FIG. 2B shows a detail drawing of a gastric and/or intestinal sleeve device with valved openings 206 through the sleeve wall. Examples of valves for this application include slit and flap type valves. Alternatively, the entire gastric sleeve 200 or a portion of it can be nonporous or impermeable to act as an internal gastric bypass. FIG. 2C shows a detail drawing of a gastric and/or intestinal sleeve device with porous sections 216 in the wall of the sleeve. FIG. 2D shows a detail drawing of a gastric and/or intestinal sleeve device with slits 218 in the wall of the sleeve. FIG. 2E shows a detail drawing of a gastric or intestinal sleeve device with artificial cilia 230 on the interior of the sleeve wall. The artificial cilia 230 facilitate the flow of food through the sleeve. Artificial cilia could be created by brushing or abrading the interior surface of the sleeve in the direction of food flow. This can raise a nap in the surface of the material biased to the direction of the abrasion. Alternatively, for example, the cilia could be molded into the surface of the sleeve. Alternatively or in addition, a hydrogel coating (for example polyvinyl pyrrolidone, hydromer) or other lubricious coating (for example PHOTOLINK LUBRICIO COATING, Surmodics Inc.) may be used to facilitate the flow of food through the sleeve.

The proximal (food entry) opening of the gastric sleeve is dimensioned to correspond to the opening of the esophagus, pouch outlet or artificial stoma. The outlet of the esophagus is generally free of restrictions to food passage while pouch outlets and stomas which are in some cases configured to restrict the passage of food. These outlets or stoma are generally less than 10-40 mm in diameter and, if restricted, are typically 15 mm or less. This proximal end of the sleeve is reinforced and/or configured for attachment to the gastric wall, surgical or artificial stoma opening. This opening for attachment is preferably slightly larger than the diameter of the restricted opening. Past the attachment to the opening the sleeve itself is typically 20-40 mm in diameter with a smooth transition from the opening diameter to the main diameter. If the sleeve continues past the pylorus, at the pylorus this diameter may remain the same, or may reduce to a smaller diameter on the order of 10-20 mm. The sleeve should not be in sealing contact with the stomach wall or the pylorus to allow free passage of gastric secretions along the outside of the sleeve as described herein.

Figure 3:
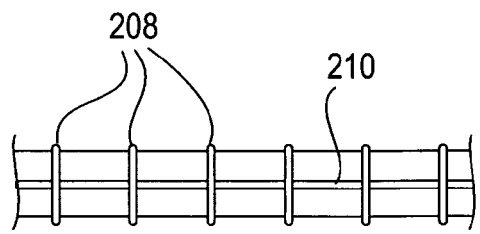
FIG. 3 shows a detail drawing of a gastric or intestinal sleeve device with reinforcement rings.
Figure 4:
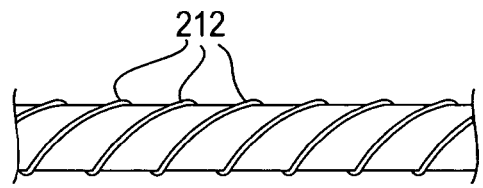
FIG. 4 shows a detail drawing of a gastric or intestinal sleeve device with a spiral reinforcement.

In certain embodiments, the wall of the gastric sleeve 200 is flexible to allow the peristaltic motions of the stomach to effect movement of food through the gastric sleeve 200. For example, blow molded 90A durometer polyurethane of a wall thickness on the order of 0.005" will work in this manner. Other suitable materials for construction of the gastric sleeve device 200 can include fluoropolymers, silicone and polyurethane. Some fluoropolymers can be thermoformed (e.g. PFA and FEP) while others such as PTFE can be expanded in a similar manner to the formation of a vascular graft as well known in that art. Silicone (e.g. Dow Silastic or similar material from Nusil Technologies) or polyurethane (e.g. Dow Pellethane) can be dip molded or cast. Polyurethane can also be blow molded. In some embodiments the wall of the sleeve may be reinforced with rings or a spiral made of wire and/or plastic to hold the sleeve open. FIG. 3 shows a detail drawing of a gastric and/or intestinal sleeve device with reinforcement rings 208. The reinforcement rings 208 are spaced apart at intervals along the length of the sleeve and the sleeve may include one or more longitudinal ribs 210 linking the reinforcement rings together along the length of the sleeve. FIG. 4 shows a detail drawing of a gastric and/or intestinal sleeve device with a spiral reinforcement 212. The reinforcement rings 208 or spiral reinforcement 212 should be resilient enough that peristaltic motions of the stomach and/or intestines can be transmitted through the wall of the sleeve with the sleeve springing back to its full diameter after the peristaltic contractions. The resiliency of the reinforcement rings 208 or spiral reinforcement 212 also allows the sleeve to be collapsed to facilitate endoscopic placement of the device. The reinforcement rings 208 or spiral reinforcement 212 may be made of or supported with stainless steel or a superelastic, or shape-memory NiTi alloy. The reinforcement rings 208 or spiral reinforcement 212 can also be plastic. The reinforcement rings 208 or spiral reinforcement 212 may be sized to fit loosely within the stomach or intestines or to provide a little bit of contact force to create a seal with the intestinal walls. As described herein in relation to the intestinal sleeve, it is important to control the coupling of forces that are transmitted by the action of the stomach (in this case) to the sleeve. Transmission of excessive force to the stomach attachment can be contraindicated in many clinical situations and in this case the coupling should be minimized. This can be accomplished, for example, through the use of low friction coatings on the sleeve exterior, using soft compliant (e.g <70A durometer non-metal reinforced) reinforcing rings and/or by not using reinforcing rings.

The interior and exterior of the sleeve can optionally be coated with a low friction material as described herein (e.g. a hydrogel) to reduce friction of food passage (interior) and reduce gastric irritation (exterior). The interior of the sleeve can optionally include flexible prongs angled toward the direction of food flow to act as artificial cilia and resist food moving retrograde along the sleeve, as shown in FIG. 2E. Optionally the distal end of the gastric sleeve can incorporate an enlarged reservoir portion proximal to the pylorus. Optionally the sleeve can include coatings on its interior and/or exterior to enhance the surface properties of the sleeve in clinically relevant manners. Coating examples include: 1) parylene coatings to increase the chemical resistance of a sleeve material, 2) coating with an antimicrobial agent to resist infection and/or 3) coating with an anti-inflammatory agent to reduce tissue inflammatory response, as described herein.

In conjunction with the gastric sleeve 200, the volume of the stomach can be reduced by suturing, stapling or banding using open, transesophageal or laparoscopic techniques. In the example shown in FIG. 1, a vertical line of gastroplasty sutures or staples 104 parallel to the sleeve 200 has been used to reduce gastric volume. Alternatively or in addition, a horizontal line of gastroplasty sutures or staples may be used to form a reduced volume gastric pouch. The sutures or staples may or may not be in a continuous line and may or may not be reversible. The stomach can also optionally be divided at the gastroplasty. These adjunctive techniques may assist in enhancing the effect of peristaltic motions of the stomach for moving food through the gastric sleeve.

Alternatively or in addition, a gastric balloon or other volume displacement device may be used in conjunction with the gastric sleeve to provide a feeling of satiety.

Preferably, portions of the gastric sleeve are constructed with radiopaque and/or sonoreflective materials and/or includes one or more radiopaque and/or sonoreflective markers for enhanced imaging by X-ray, fluoroscopy and/or ultrasonic imaging so that the position and functional state of the implanted gastric sleeve can be verified noninvasively. However, the sleeve should not be completely radiopaque to allow visualization of the passage of ingested radioopaque contrast as in a "swallow" study.

Figure 5:
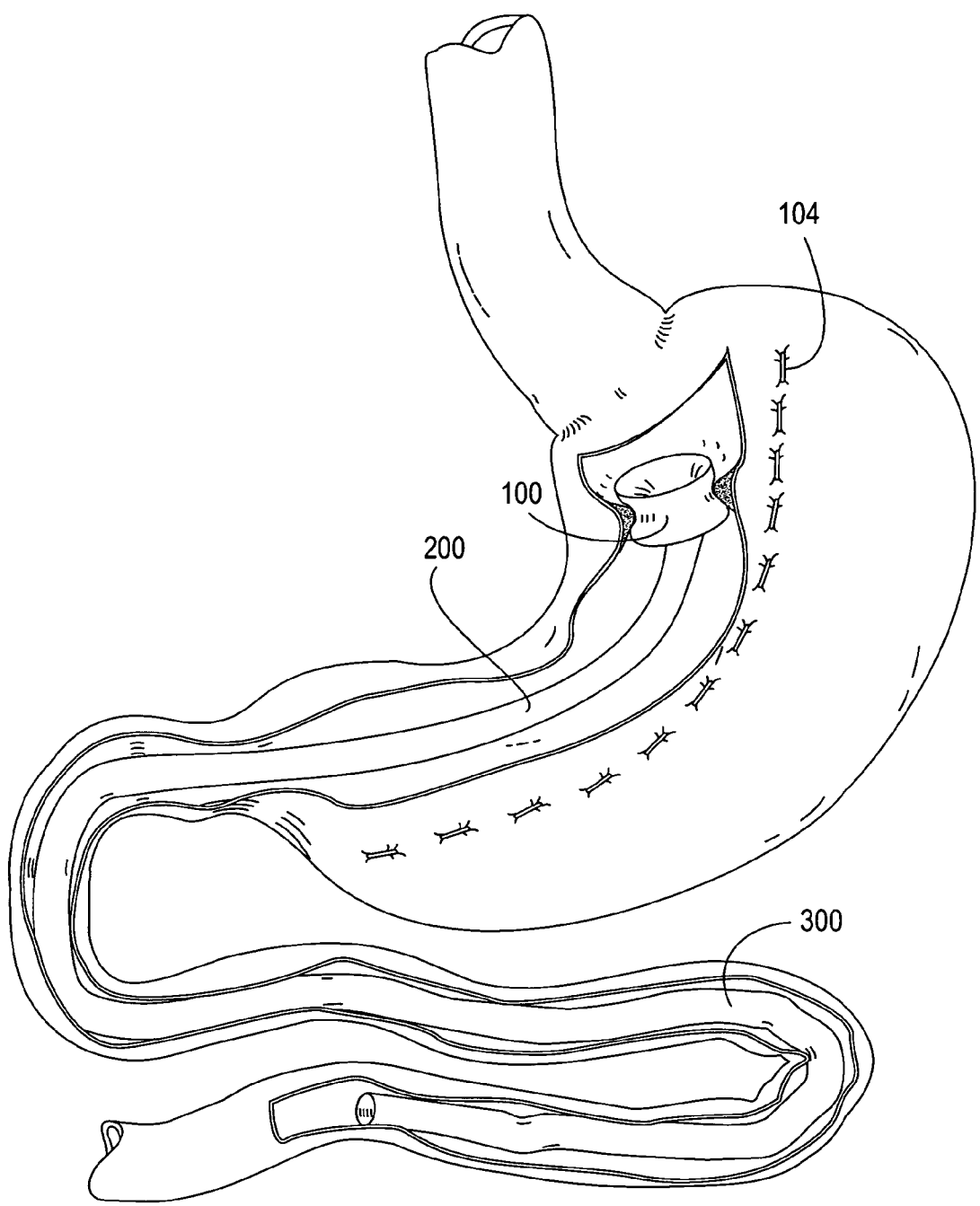
FIG. 5 shows a combined gastric and intestinal sleeve device with an artificial stoma device implanted within a patient's stomach with a line of gastroplasty sutures or staples parallel to the sleeve.

In another aspect, the system may include an internal intestinal sleeve 300 that may be used separately or used with, attached to or integrated with the internal gastric sleeve 200 and artificial stoma component 100. FIG. 5 shows a combined gastric 200 and intestinal 300 sleeve device with an artificial stoma device 100 implanted within a patient's stomach with a line of gastroplasty sutures or staples parallel to the sleeve 104. The entire intestinal sleeve 300 or a portion of it can be porous or semipermeable to allow the flow of digestive secretions into the sleeve and to allow the flow of nutrients and/or fluids out through the wall of the sleeve. Suitable materials for construction of the intestinal sleeve device 300 include fluoropolymers, silicone (e.g. Dow Silastic or similar material from Nusil Technologies) and polyurethane (e.g. Pellethane). For example, in one embodiment the intestinal sleeve device 300 may be constructed of blow molded 90A durometer polyurethane with a wall thickness on the order of 0.005". Some fluoropolymers can be thermoformed (e.g. PFA and FEP) while others such as PTFE can be expanded in a similar manner to the formation of a vascular graft as well known in that art. Openings 204 may be provided through the wall of the sleeve, as shown in FIG. 2A. Valves 206 may be provided in the wall of the intestinal sleeve to allow digestive secretions to enter the sleeve, but to prevent solid food and/or nutrients from flowing out through the wall of the sleeve, as shown in FIG. 2B. Alternatively, the entire intestinal sleeve or a portion of it can be nonporous or impermeable to act as an internal intestinal bypass. Valve and porosity structures to allow flow such as those described herein in relationship to the gastric sleeve can also be applied to the intestinal sleeve. In certain embodiments, the wall of the intestinal sleeve 300 is flexible to allow the peristaltic motions of the intestinal wall to effect movement of food through the intestinal sleeve. The interior and exterior of the sleeve can optionally be coated with a low friction material (e.g. a hydrogel) to reduce friction of food passage (interior) and reduce intestinal irritation (exterior). Other coatings such as those described herein in relationship to the gastric sleeve can also be applied to the intestinal sleeve. The interior of the sleeve can optionally include flexible prongs angled toward the direction of food flow to act as artificial cilia and resist food moving retrograde along the sleeve, as shown in FIG. 2E. The wall of the sleeve may be reinforced with rings 208 or a spiral 212 made of wire and/or plastic, as shown in FIGS. 3 and 4. Optionally the intestinal sleeve can include means for stabilization at the distal end such as a brush (as described by Berry), weight or inflatable balloon.

The intestinal sleeve diameter can be 10-40 mm, but it is typically 15-30 mm with an optional smaller diameter at the point the sleeve passes through the pylorus (if the sleeve passes through the pylorus). The diameter of the sleeve is optionally selected to be smaller than the diameter of the intestine. The sleeve should not be in permanent sealing contact with the intestinal wall or the pylorus if it is intended to control or allow passage of gastric, biliary, pancreatic and intestinal secretions along the outside of the sleeve.

Figure 6:
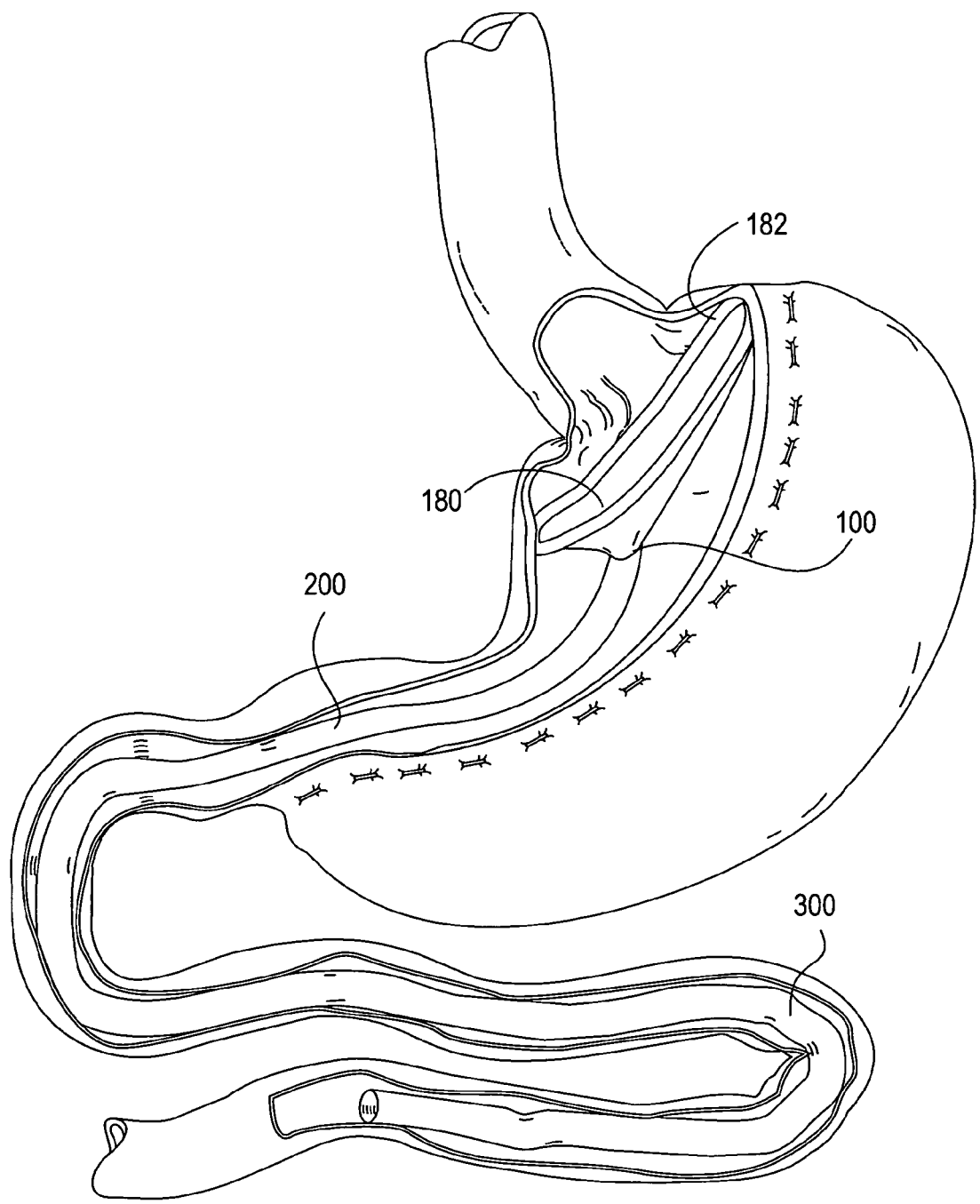
FIG. 6 shows a combined gastric and intestinal sleeve device with an artificial stoma device located within a funnel-shaped entry with a reinforced suture area.

Optionally, the intestinal sleeve 300 may have a proximal end with a reinforced anchoring segment or other anchoring mechanism for attachment in the region of the pylorus or the proximal end of the intestinal sleeve 300 may be attached to a stoma device or surgically created stoma at the outlet of a reduced stomach. Alternatively, the intestinal sleeve 300 may be attached to or continuous with the internal gastric sleeve 200. Optionally, the distal end of the intestinal sleeve 300 may include an anchoring mechanism. FIG. 6 shows a combined gastric 200 and intestinal 300 sleeve device with an artificial stoma device 100 located within a sleeve entry 180 with a reinforced suture area 182. The sleeve entry 180 creates a reduced-volume pouch within the patient's stomach that functions similarly to a surgically created gastroplasty pouch.

The intestinal sleeve 300 is typically approximately 60-180 cm in length, whereby partially digested or undigested nutrients exit from the sleeve into the jejunum where they can elicit a hormonal, neural and/or osmotic reaction in the jejunum and/or ileum. However, sleeve length can be either shorter or longer depending on clinical needs. Increasing the length of the sleeve can increase the degree of response in the ileum while reducing the length of the sleeve can have the opposite effect.

In relation to the example of the placement of a stoma 100 implanted into a surgically formed pouch described above, the gastric sleeve 200 and/or intestinal sleeve 300 may be implanted according to the following method:

Preferably, portions of the intestinal sleeve are constructed with radiopaque and/or sonoreflective materials and/or includes one or more radiopaque and/or sonoreflective markers for enhanced imaging by X-ray, fluoroscopy and/or ultrasonic imaging so that the position and functional state of the implanted intestinal sleeve can be verified noninvasively. However, the sleeve should not be completely radiopaque to allow visualization of the passage of ingested radioopaque contrast as in a "swallow" study.

Figure 7:
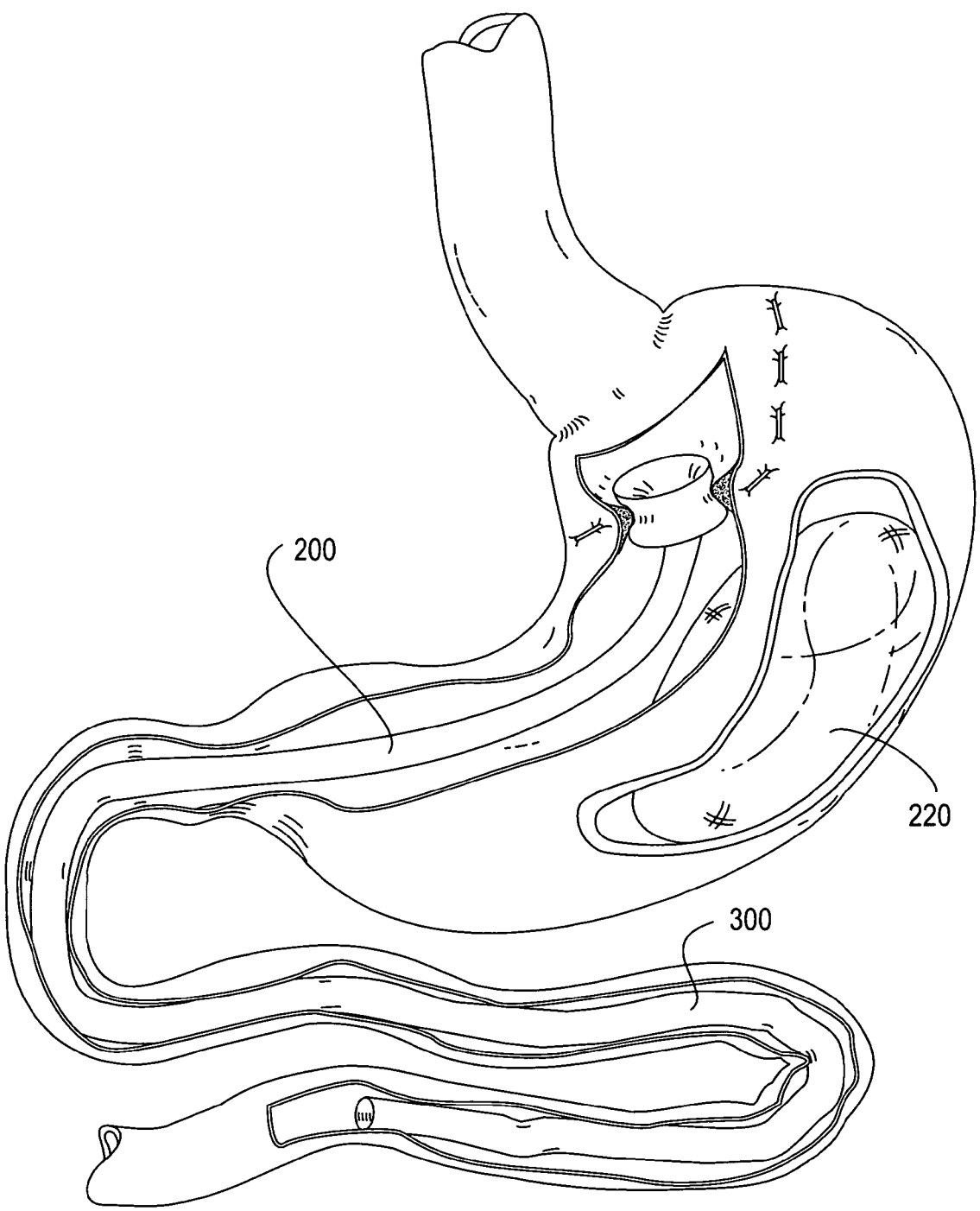
FIG. 7 shows a combined gastric and intestinal sleeve device implanted within a patient's stomach with a gastric balloon to reduce the gastric volume.

FIG. 7 shows a combined gastric 200 and intestinal 300 sleeve device implanted within a patient's stomach with a gastric balloon 220 to reduce the gastric volume.

In summary, one aspect of the invention provides a method and system for treatment of morbid obesity that has three components, an artificial stoma device, an internal gastric sleeve and an internal intestinal sleeve, which can be used separately or in combination. The artificial stoma device is implanted into a patient's stomach or lower esophagus and then can optionally be used to restrict food intake. The artificial stoma device may have a fixed aperture, an adjustable aperture or an aperture that varies in response to changing stomach conditions. The artificial stoma device may be implanted using sutures, staples, a reinforced anchoring segment, a sutureless or other attachment mechanism as described herein. A restriction can optionally be placed within the lumen of the gastric sleeve. The internal gastric sleeve may be separate from or integrated with the artificial stoma device. The internal gastric sleeve effectively reduces the patient's gastric volume and restricts the absorption of nutrients and calories from the food that passes through the stomach. The internal intestinal sleeve may be separate from or integrated with the internal gastric sleeve and/or the artificial stoma device. The wall of the internal gastric sleeve and/or internal intestinal sleeve may be constructed with reinforcing rings or a spiral reinforcement. The wall of the internal gastric sleeve and/or internal intestinal sleeve may have openings or valves to allow or restrict the digestive secretions and nutrients through the wall of the sleeve.

The method provided by this invention has the capacity to combine these various components, as well as other components described herein, into a system that treats obesity by creating a pouch with an outlet restriction which can be optionally controlled or operable, placing means by which the food exiting the pouch is transferred via gastric and intestinal sleeves to a point in the intestine while being substantially isolated from (or allowed to contact a controlled amount) gastric, biliary, pancreatic and intestinal secretions, whereby this location in the intestine can be optionally selected to induce various reactions of the intestinal tissue which may include dumping syndrome, hormonal secretion and/or nervous stimulation.

In contrast to previous devices, the present inventors have found that in many cases an effective gastrointestinal sleeve device will preferably have the characteristics of each section of the device tailored to the function of the section of the gastrointestinal tract in which it resides. For example, in some clinical situations a potential issue with gastric pouch or sleeve systems could be a lack of physiological signals causing opening of the pylorus. If the pylorus were to remain tightly closed over a sleeve passing through, it could be problematic for the patient. In these clinical situations, one desirable characteristic of an effective gastrointestinal sleeve device could be for it to have sufficient volume and/or compliance in the area of the stomach immediately upstream of the pylorus to create enough pressure or wall tension in that area to trigger the opening of the pylorus to empty the stomach contents.

In addition, when normal functioning of the pylorus is clinically desired, the section of the sleeve device that passes through the pylorus must have enough wall flexibility or compliance to allow normal opening and closing of the pylorus and to allow drainage of stomach secretions around the outside of the sleeve. For example blow molded 90A durometer polyurethane of a wall thickness on the order of 0.005" or less will work in this manner. Other sections of the gastrointestinal sleeve device will also be tailored to the section of the gastrointestinal tract in which it resides.

The configuration of the gastrointestinal sleeve device enables a method of treatment for morbid obesity that includes isolating ingested food from the digestive secretions of the stomach and intestines as the food passes through the stomach, the duodenum and the upper part of the jejunum.

Figure 8:
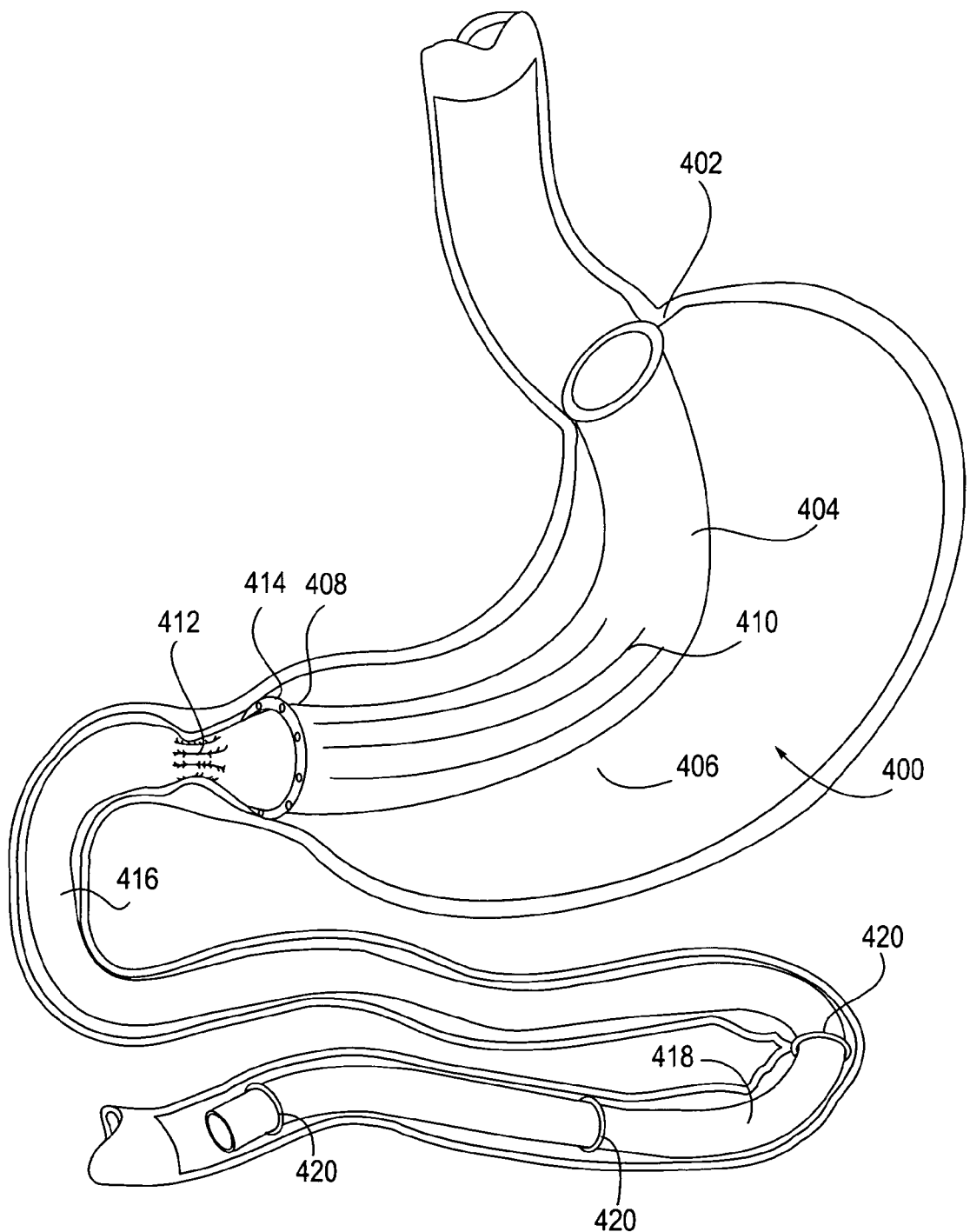
FIG. 8 illustrates an example of a gastrointestinal sleeve device deployed within a patient's gastrointestinal tract for treating morbid obesity.

FIG. 8 illustrates an example of a gastrointestinal sleeve device 400 constructed in accordance with the present invention. The gastrointestinal sleeve device 400 is shown deployed within a patient's gastrointestinal tract for treating morbid obesity. The characteristics of each portion or section of the gastrointestinal sleeve device 400 may be tailored to the function of the section of the gastrointestinal tract in which it resides.

The proximal opening 402 of the gastrointestinal sleeve device 400 is primarily designed to facilitate attachment of the sleeve within the patient's stomach. Depending on the clinical needs of the individual patient and the judgement of the physician, locations for attachment of the proximal opening 402 of the sleeve may include the gastroesophageal junction and the cardia or cardiofundal border. The gastroesophageal junction is advantageous as a possible attachment site because the tissue wall is relatively thick at this location and it is relatively easy to access via a peroral route. Attachment at the gastroesophageal junction excludes all gastric secretions from the interior of the gastrointestinal sleeve device 400. The cardiofundal border is also advantageous as a possible attachment site because it provides the ability to create a gastric pouch from the cardia of the stomach and the tissue wall is relatively thick at this location compared to the fundus. Attachment at the cardia or cardiofundal border allows the secretions of the cardia, which are primarily lubricious mucous, to enter the interior of the gastrointestinal sleeve device 400 and excludes the fundal secretions, which are high in acid content, from the interior of the sleeve. The lubricious mucous secretions from the cardia will help to lubricate the interior surface of the gastrointestinal sleeve device 400 and will facilitate passage of ingested food through the sleeve.

By way of example, the embodiment of FIG. 8 shows the proximal opening 402 of the gastrointestinal sleeve device 400 attached at the gastroesophageal junction. In this configuration, it can be preferred that the proximal opening 402 be sized to have a diameter approximately equal to, or slightly larger than the diameter of the esophagus at the gastroesophageal junction. In adult humans, the esophagus at this point typically has a diameter of approximately 1.5-2.0 cm.

Attachment of the proximal opening 402 of the gastrointestinal sleeve device 400 within the stomach can be accomplished using open, laparoscopic or endoscopic surgical techniques e.g. sutures, wires or staples or using any of the attachment methods described herein. Attachment is preferably optimized to distribute stress over an enlarged area and minimize stress or strain transmitted to the tissue where it is attached in order to minimize tissue erosion. During ingestion of food, the sleeve and the attachment must withstand the pressure created by swallowing as the food is forced into the sleeve. This is particularly true if there is a restriction downstream of the proximal sleeve opening. The sleeve and the attachment must also withstand any tensile forces created as a result of swallowing food and the presence of any food or liquid within the sleeve or pouch, as well as forces due to peristaltic action of the intestines or stomach.

Figure 9A:
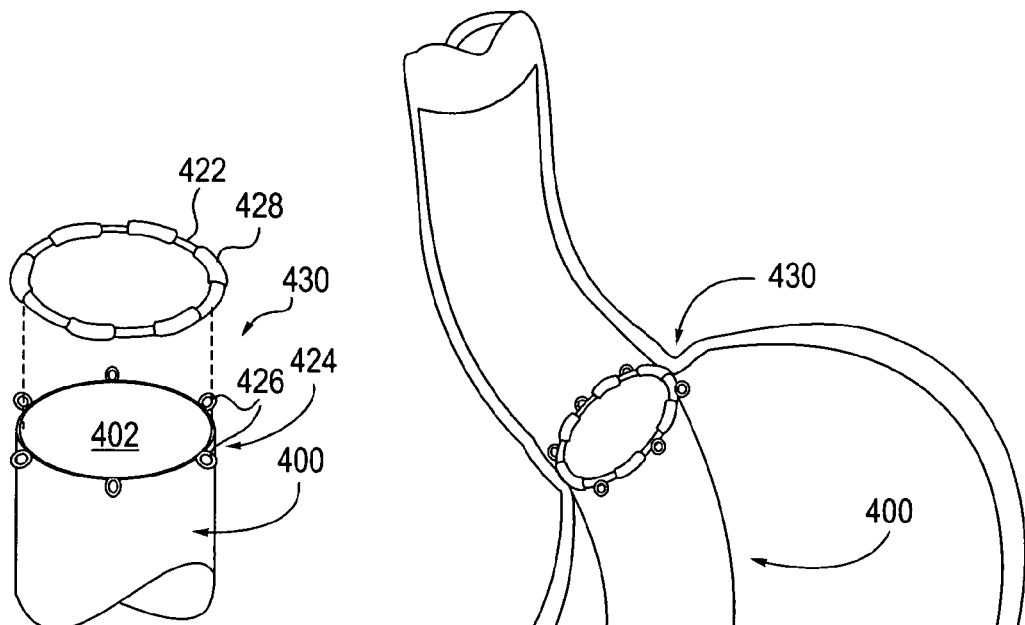
FIGS. 9A and 9B illustrate a gastrointestinal sleeve device with a healable, removable fixation system.
Figure 9B:
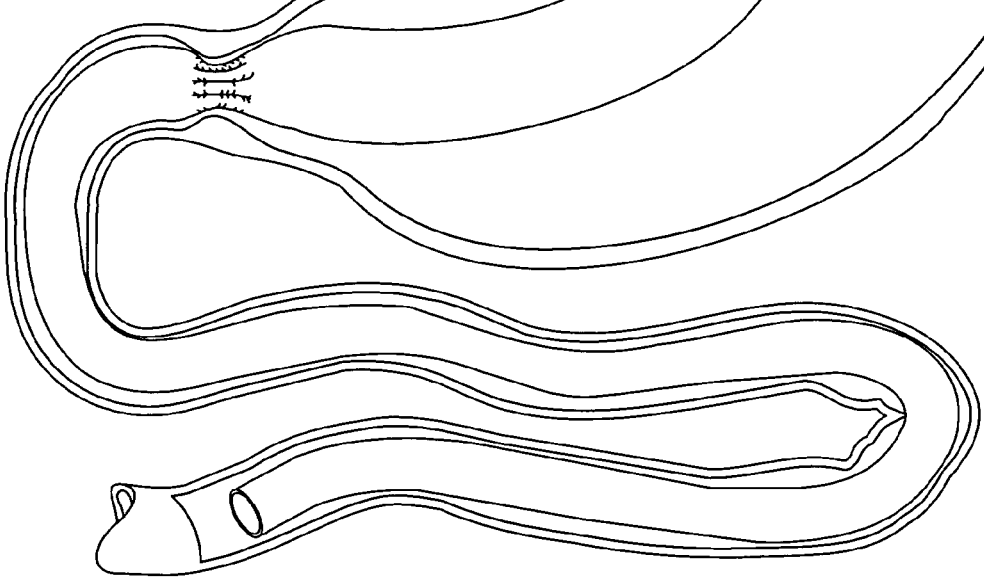

In one embodiment shown in FIGS. 9A and 9B, the proximal opening 402 of the gastrointestinal sleeve device 400 is attached to the stomach wall with an optionally removable, healable fixation system 430. The fixation system 430 is configured with two components: an anchor ring 422 and an attachment means 424 for connecting the gastrointestinal sleeve device 400 to the anchor ring 422. The attachment means 424 could be configured as part of the anchor ring 422 or the gastrointestinal sleeve device 400 or as one more separate components. The fixation system 430 is configured to operate in three different modes. It can provide a permanent or long-term attachment of the gastrointestinal sleeve device 400 to the stomach wall; it can allow replacement or revision of the gastrointestinal sleeve device 400 without removal of the anchor ring 422; and it can be removed completely to allow the stomach wall to heal where the anchor ring 422 had been attached.

The anchor ring 422, shown in FIG. 9A, may be configured as a continuous wire, polymer or wire-reinforced polymer ring with an exterior or coating that resists ingrowth and adhesion. The wire could be NiTi or SS. Suitable polymers would include silicone, Teflon (PTFE) and other fluoropolymers. Possible coatings include hydrophilic coatings, hydromers, hydrogels and fluoropolymers. Portions of the anchor ring 422 can be enclosed with a material 428 that encourages ingrowth of tissue. Between the portions of ingrowth material 428, the anchor ring 422 can be bare to discourage ingrowth and to provide attachment points for the gastrointestinal sleeve device 400. The ingrowth material 428 in this embodiment is preferably a biodegradable or resorbable material such as polyglecaprone (Monocryl, Ethicon), polyglactin (Vycril, Ethicon), or other known biodegradable or resorbable material. The ingrowth material 428 is configured so ingrowth results in a partial and intermittent encapsulation of the anchor ring 422. Areas of encapsulation would be interspaced with areas where ring was exposed.

In one example of the fixation system 430 shown in FIG. 9A, the attachment means 424 is configured with a plurality of clip rings 426 mounted around the exterior of the gastrointestinal sleeve device 400 near the proximal opening 402. The clip rings 426 are configured with gaps in the rings that allow the rings to clip onto the exposed bare portions of the anchor ring 422 to hold the gastrointestinal sleeve device 400 in position. In other embodiments, the attachment means 424 may comprise magnets, clips, hooks, staples, sutures or other known fasteners.

In one method, the anchor ring 422 would be implanted and allowed to heal before another device, such as the gastrointestinal sleeve device 400, would be attached to it. After sufficient healing has taken place, the device could be attached to the anchor ring at areas where ingrowth did not occur, as shown in FIG. 9B. In this method/structure a biodegradable ingrowth material is used and since the ingrowth material is biodegradable, it will eventually disappear after providing a scaffold for ingrowth resulting in intermittent encapsulation of the anchor ring.

FIG. 9B also shows no restriction at the attachment stoma and no restriction in the sleeve thereby showing the pylorus acting as a naturally controlled restriction as described herein.

In another example of an alternate embodiment the sleeve of FIG. 9B could use an attachment ring and ring interface which are attached to the stomach using T-tag fasteners or T-pledgets as described in U.S. patent application Ser. No. 10/698,148.

The anchor ring and the gastrointestinal sleeve device 400 can be left in place permanently. Alternatively, the gastrointestinal sleeve device 400 can be removed at a later date and replaced or revised. If and when it is desirable to remove the anchor ring, one or more or areas with no ingrowth can be used as access to sever or cut the ring. Since the ring exterior resists ingrowth and is nonadherent, it can be pulled out of the tissue without damaging the tissue. After removal of the anchor ring, the tunnel through the tissue formed by the encapsulation can heal.

As an alternative to a biodegradable material, a nondegradable scaffold material can be used. These materials become incorporated into tissue and are often made of naturally occurring or biological components, such as processed bovine tissue.

Figure 10A:
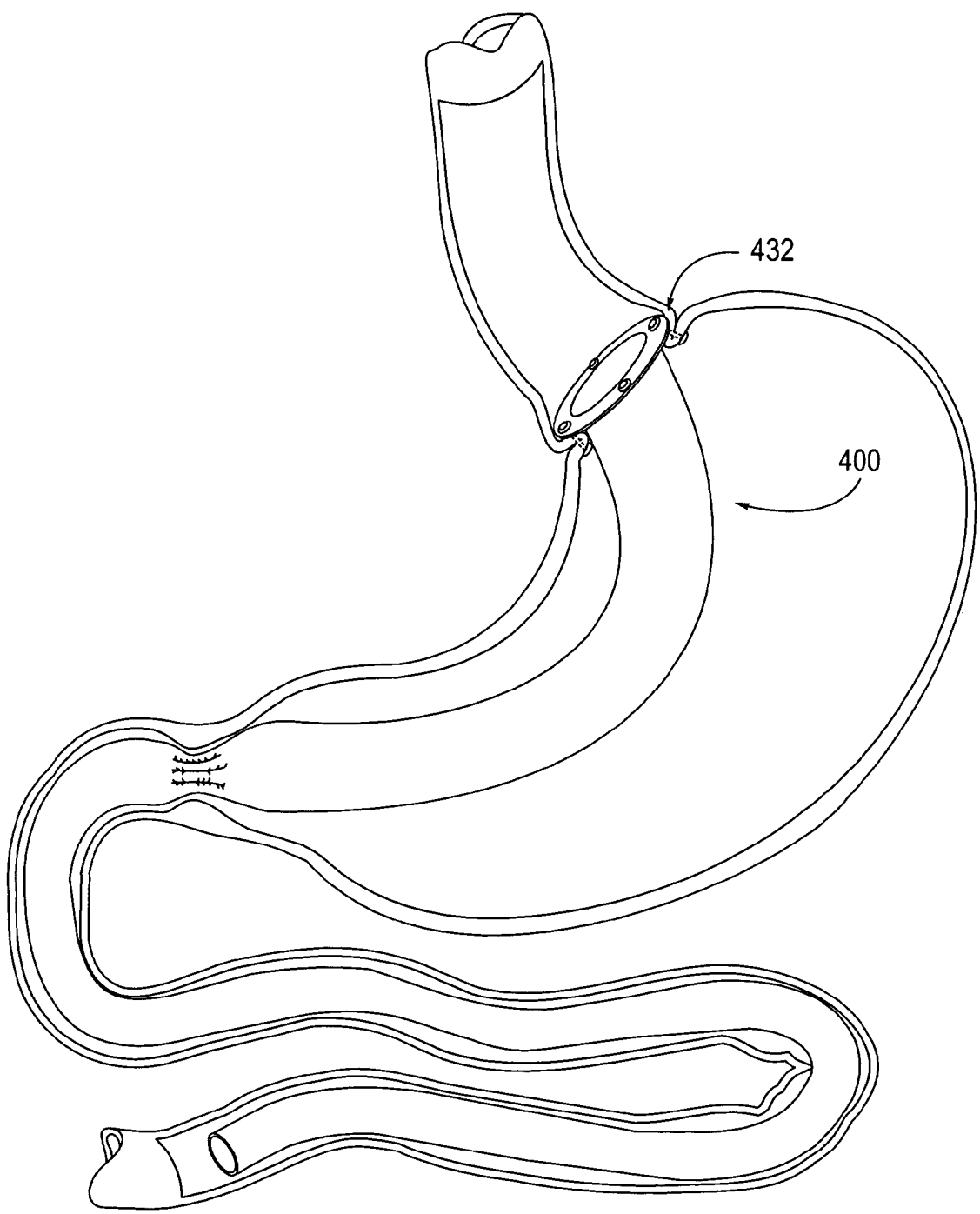
FIGS. 10A-10D illustrate various gastrointestinal sleeve devices attached within a patient's stomach.

FIG. 10A shows another way of attaching the proximal opening 402 of the gastrointestinal sleeve device 400 within the patient's stomach. A combined attachment/stoma device 432 is implanted into the patient's stomach to create a restriction and the gastrointestinal sleeve device 400 is attached to the stoma device. The stoma device 432 and the gastrointestinal sleeve device 400 may be implanted in a single procedure or they may be implanted in two sequential procedures as described above, leaving enough time for healing of the gastric wall in between the two procedures. The stoma device 432 may be attached at the gastroesophageal junction or it may be attached at the cardiofundal border to create a reduced volume reservoir upstream of the restriction (gastric pouch) using the tissue of the cardia, as shown in FIG. 10A. The gastrointestinal sleeve device 400 may be attached using any one of the stoma devices described herein. By way of example, the gastrointestinal sleeve device 400 of FIG. 10A is shown attached using a stoma device 432 in the form of a stomal ring clip.

In general, the proximal end of the gastrointestinal sleeve device 400 may be secured in the vicinity of the lower esophageal sphincter or z-line, using a stoma device 432 having any of a variety of configurations including those illustrated in FIGS. 10A-D. As used herein, the term "stoma device" includes devices which define an opening, without limitation to the relative size of the opening compared to the surrounding anatomy unless otherwise described.

Figure 10B:
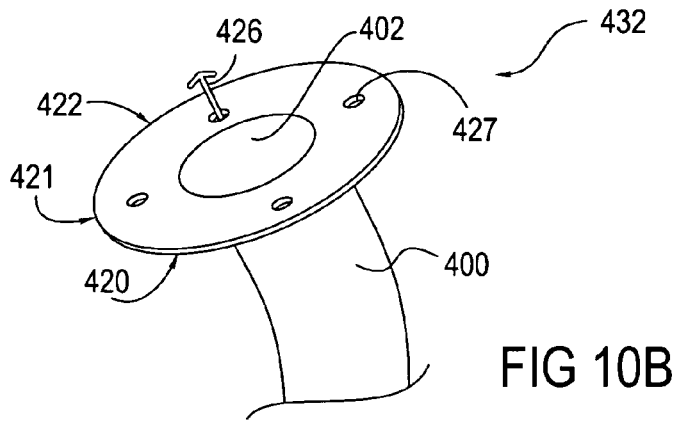
Figure 10C:
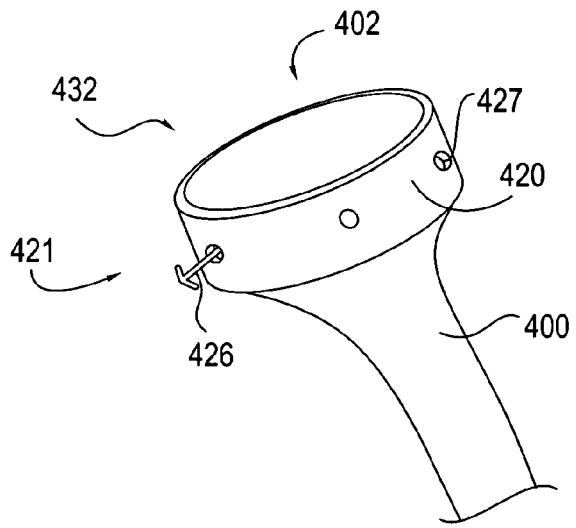

Referring to FIGS. 10A and 10B, the stoma device 432 includes at least one tissue contacting surface 420 for contacting tissue such as illustrated in FIG. 10A. The tissue contacting surface 420 may be carried by an anchor support 421 such as a transverse flange 422. In the illustrated embodiment, the transverse flange 422 comprises a continuous radially outwardly extending annular support. However, the anchor support 421 may comprise a plurality of radially outwardly extending connection tabs such as two or four or six or eight or more, which may be circumferentially symmetrically positioned about the longitudinal axis of the gastrointestinal sleeve 400. As is described elsewhere herein, the gastrointestinal sleeve 400 may be either permanently or detachably connected to the anchor support 421. The anchor support 421 may be provided with a plurality of apertures 427 such as to receive a "T" fastener or other tissue connector. Alternatively, the anchor support 421 may be pierceable by the deployment of the "T" fastener or other tissue connector.

In a modification of the anchor support 421 (see FIG. 10C), the at least one tissue contacting surface 420 faces radially outwardly from the longitudinal axis of the gastrointestinal sleeve 400. In this configuration, the "T" fastener or other tissue anchor may extend radially outwardly into adjacent tissue, as may be desirable depending upon the tissue anchor configuration. The tissue contacting surface 420 may also be inclined with respect to the longitudinal axis of the gastrointestinal sleeve 400.

Figure 10D:
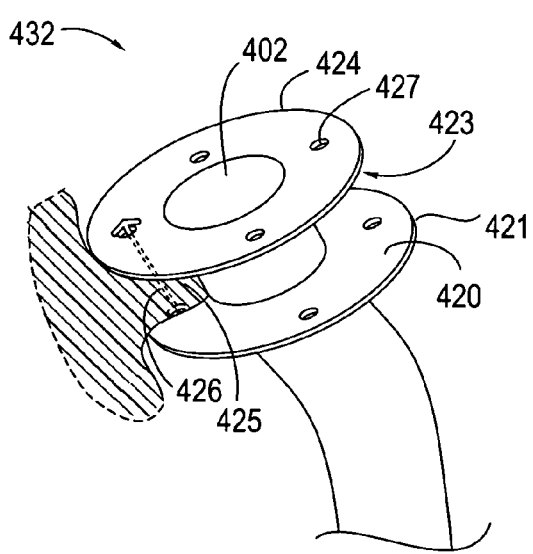

Referring to FIG. 10D, at least a first tissue contacting surface 420 is carried by a first anchor support 421 and at least a second tissue contacting surface 423 is carried by at least a second anchor support 424. In the illustrated embodiment, each of the first anchor support 421 and second anchor support 424 is illustrated as an annular flange. However, the anchor supports may take any of a variety of configurations as has been discussed. In addition, the first anchor support 421 and second anchor support 424 are spaced axially apart, to allow tissue 425 to be drawn therebetween. Tissue 425 may be drawn between the first and second anchor supports using vacuum, supplied by the deployment catheter. This configuration enables the advance of a fixation device 426 between the first anchor support 421, through the tissue 425 and into or through the second anchor support 424 as illustrated in FIG. 10D. The device shown in FIG. 10D can optionally be configured to enable full thickness plication and serosa-to-serosa contact at the fixation device 426 as described herein. The fixation device 426 may comprise a "T" fastener, a pin, or other structures disclosed herein. In the annular construction illustrated in FIG. 10D, two or four or more tissue extensions 425 may be drawn radially inwardly, for attachment to the stoma device 432.

The attachment described in FIG. 10A can also be used where the attachment is dimensioned so as not to create a restriction. In this case, a restriction can optionally be placed downstream within the gastric sleeve. It is generally clinically preferable for devices placed at the gastroesophageal junction to have the stoma downstream, while devices placed at the cardiofundal border may combine the restriction with the attachment to allow a smaller food reservoir upstream of the restriction.

Downstream of the proximal opening 402, the gastrointestinal sleeve device 400 has sleeve portions 404, 406 that reside in the fundus and the antrum of the stomach, respectively. In the example of FIG. 8, the gastrointestinal sleeve device 400 has an approximately constant diameter from the proximal opening 402 to the upstream end 408 of the pylorus, including the fundus portion 404 and the antrum portion 406 of the sleeve. In this embodiment, the sleeve through the fundus and antrum portions 404, 406 preferably has a diameter approximately equal to or slightly larger than the diameter of the esophagus at the gastroesophageal junction, which in adult humans is approximately 1.5-2.0 cm. Alternatively, the gastrointestinal sleeve device 400 may gradually taper outward or open immediately downstream of the proximal opening 402. In this embodiment, the gastrointestinal sleeve device 400 preferably has a proximal opening 402 with a diameter of approximately 1.0-1.5 cm where it is attached to the stoma device 432. Downstream of the proximal opening 402, the fundus and antrum portions 404, 406 of the sleeve have a diameter of approximately 1.5-2.0 cm.

The example illustrated in FIG. 10A may utilize any of a variety of dimensions, materials, attachment structures and other features disclosed elsewhere herein. In general, the example of FIG. 10A is provided with a substantially uniform inside diameter throughout its axial length. Axial lengths between the proximal opening 402 and a distal end of the device are generally in excess of 50 cm, often at least about 75 cm to 125 cm or more, depending upon the desired clinical performance as has been described elsewhere herein. In one implementation of the invention, the tubular wall of the gastrointestinal sleeve 400 is sufficiently flexible that the natural operation of the pylorus operates as an adjustable stoma on material traveling through the sleeve 400.

The sleeve 400 may be attached in the vicinity of the gastroesophageal junction, such as by attachment to a ring or cuff or directly attached to the cardia of the stomach adjacent the gastroesophageal junction. Attachment may be accomplished in any of a variety of ways including those disclosed elsewhere herein.

The sleeve 400 may comprise a homogenous material throughout. At least the gastric section may comprise a sufficient length to extend through the gastroesophageal junction, past the pylorus and into the duodenum. Materials such as a blow molded polyurethane, having a wall thickness of approximately 0.005" and a durometer of about 90A may be used. The sleeve 400 may additionally be provided with a lubricious coating on one or more of the interior and exterior surfaces. Diameters on the order of about 2.0 cm±50% or more may be utilized. Other dimensions and materials may be optimized by those of skill in the art in view of the disclosure herein.

The intestinal section of the sleeve 400 is dimensioned to start in the duodenum and extend at least about 50, often about 75 or 100 cm or more, to imitate a gastric bypass. The intestinal section of the sleeve 400 may be the same diameter as the gastric portion of the sleeve, or may be no more than about 90% or 80% or less of the diameter of the gastric sleeve portion. Delivery and retrieval techniques for the implementation of the invention illustrated in FIG. 10A have been disclosed elsewhere herein.

The function of the sleeve portion 404 located in the zone of the fundus is to transmit food through the gastrointestinal sleeve device 400. Accordingly, this portion of the gastrointestinal sleeve device 400 may be configured to resist kinking and provide a lubricious inner surface. Saliva and mucous secreted in the esophagus and/or cardia could facilitate passage of food. The zone of the fundus and/or the area of the cardiofundal border could be a possible location for a restriction if one is used. Location of the restriction is clinically relevant in that the volume between the restriction and the gastroesophageal junction effectively defines a restricted stomach volume.

The antrum of the stomach has muscular action to grind food and this muscular action can manifest as peristalsis. Based upon clinical requirements, the sleeve portion 406 in the antral zone could include stiffening members 410 or other means to prevent motion and/or kinking of the sleeve. The stiffening members 410, which may be made of a metal and/or polymer, may be oriented axially, as shown in FIG. 8, or they may be in a helical configuration or other geometry. This reinforcing should be configured so as to provide little or no interface for peristaltic motion to capture the sleeve and move it toward the pylorus. The sleeve should also be configured to resist or avoid forces that could be applied in a retrograde direction. Note that the retrograde force is caused by fluid flow. As the antrum undergoes peristalsis, food and secretions can flow retrograde. A slippery hydrophilic or other coating, as described herein, on the exterior of the sleeve in the antrum portion 406 may be preferred.

Figure 11:
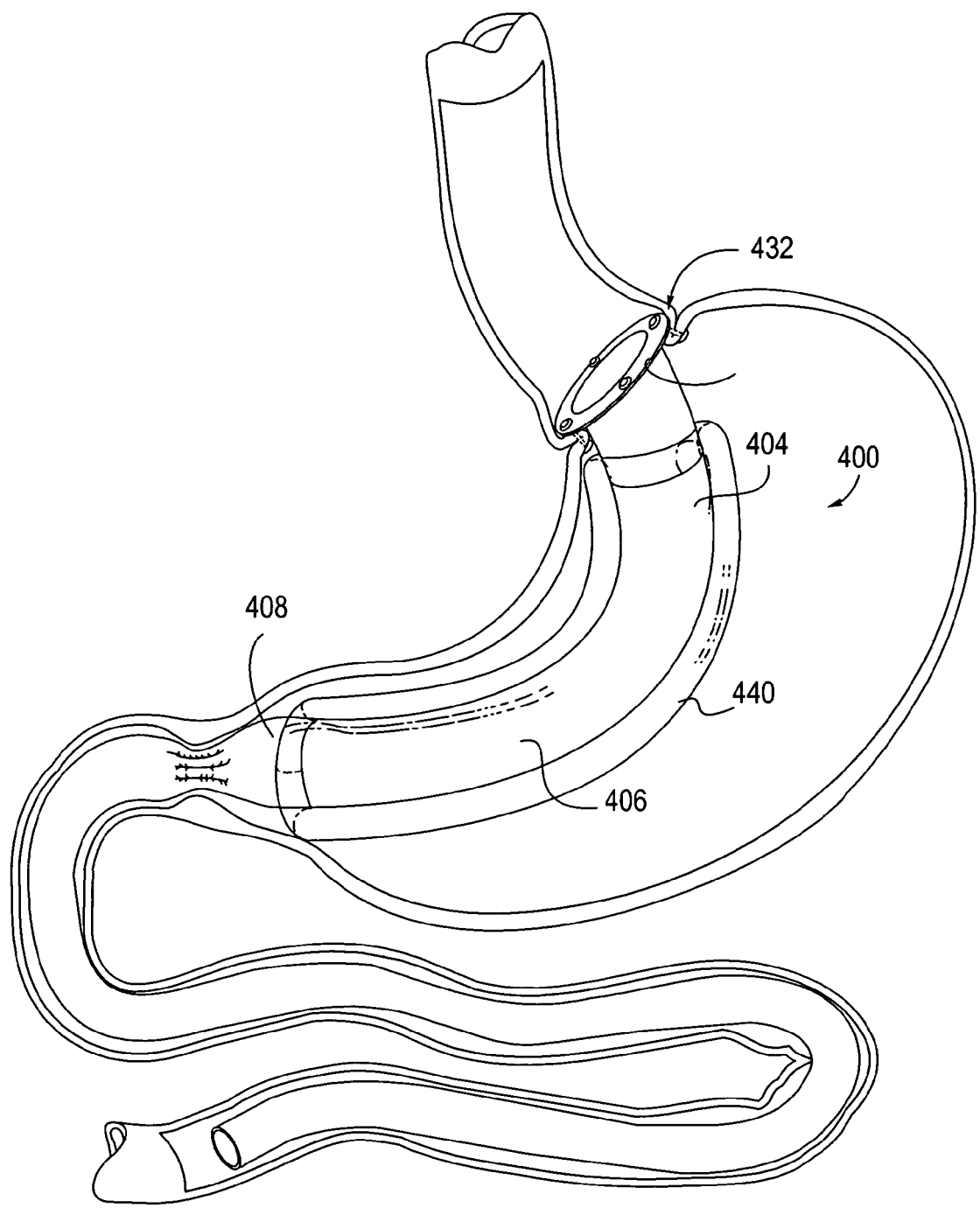
FIG. 11 illustrates a gastrointestinal sleeve device with a coaxial inflatable balloon surrounding the sleeve within the patient's stomach.

In an alternate construction illustrated in FIG. 11, the fundus portion 404 and/or the antrum portion 406 of the gastrointestinal sleeve device 400 may be stiffened using a coaxial inflatable balloon 440 that surrounds the sleeve. The coaxial balloon 440 may be inflated within the patient's stomach using a detachable tether and a self-sealing valve as described in the prior art (e.g. Pevsner). With proper selection of inflation media (compressible air or incompressible liquid) inflation pressure and inner and outer wall compliance, the coaxial balloon 440 can optionally provide axial stiffening, and can optionally serve to transmit peristaltic motion to the interior of the gastrointestinal sleeve device 400 to help ingested food transit through the sleeve.

Downstream of the antrum portion 406, the gastrointestinal sleeve device 400 may optionally include a pyloric anchor 414 at the upstream end 408 of the pylorus, as shown in FIG. 8. In one embodiment, the pyloric anchor 414 is configured as a perforated collar slidable along the exterior of the sleeve for custom fit to the patient. The outer circumference of the pyloric anchor 414 is optionally attached to the stomach lining at the upstream end 408 of the pylorus, then the slidable collar is cinched around or otherwise attached to the sleeve to anchor it in position. Perforations or channels in the collar allow gastric secretions to pass from the stomach into the pylorus without obstruction. The pyloric anchor 414 can be constructed from a variety of biocompatible materials with different properties. For example, fluoropolymers such as Teflon (Dupont) can be used to avoid ingrowth or, alternatively, polyester cuff materials (e.g. Dupont Dacron) can be used to encourage ingrowth if desired. As an alternative to attaching the pyloric anchor to the stomach wall, it can be constructed with sufficient stiffness and sized to be retained in the antrum of the stomach by being too large to pass through the pylorus.

An anchor placed in the antrum can also be used as a platform to support devices placed in the stomach. For example, combining such an anchor located in the antrum with the reinforced sleeve or coaxial balloon as described herein can be used to support an attachment ring and reduce the forces transmitted to the attachment at the stomach wall. Structures that are not a part of the gastric sleeve such as self-expanding wire meshes of NiTi or stainless steel could also be used where clinically indicated. Antral support structures could also be independent, as a sleeve anchor and could optionally be used to support other devices as described herein.

In certain embodiments, the sleeve is configured to open and to collapse as it passes through the pylorus to facilitate internal passage of food and external passage of gastric secretions and to minimize irritation and/or damage to the pylorus. Additionally, the gastrointestinal sleeve device 400 may optionally narrow slightly in diameter as it passes through the pylorus so that it facilitates passage of gastric secretions along the exterior of the sleeve through the pylorus when it is opened. This diameter may be on the order of 0.75-2.5 cm. The pylorus section 412 of the gastrointestinal sleeve device 400 must have enough wall flexibility or compliance to allow normal opening and closing of the pylorus and to avoid irritation of the pylorus. For example blow molded 90A durometer polyurethane of a wall thickness on the order of 0.005" or less will work in this manner. With this configuration one can optionally use the pylorus as a natural stoma by allowing the sleeve to be closed by the pylorus and then opened to allow passage of food when the muscles of the pylorus relax.

Conversely, in some patients it may be desirable to hold open the pylorus. In such cases where the device is configured for holding open the pylorus, it should also include means of draining gastric secretions, e.g. tubes or channels, along the exterior of the sleeve.

A collapsible or collapsed tubular gastrointestinal sleeve device can allow gastric and intestinal secretions to pass along its outer surface. Spiral reinforcing can facilitate passage of the secretions if the sleeve between the reinforcing is configured to form channels where secretions can flow between the reinforced sleeve and the wall of the intestine or pylorus with which it may be in contact. This could be of particular use in the pylorus where food in the sleeve could be competing with gastric secretions to pass through the pylorus outside the sleeve. In the case of a flaccid sleeve, whichever of the food or secretions has the higher pressure would pass through the pylorus. In the case of a spiral reinforced sleeve with channels or other means (e.g. tubular lumens passing through the pylorus and with openings both proximal and distal to the pylorus) of enabling passage of secretions along the pylorus, the food and secretions could pass at the same time.

The gastrointestinal sleeve device 400 continues below the pylorus and passes through the duodenum and into the jejunum. The duodenum portion 416 and the jejunum portion 418 may have a total length of approximately 50-200 cm, depending on the clinical needs of the individual patient and the judgement of the physician. Shorter lengths may be used if it is desirable for the sleeve to empty into the duodenum or proximal jejunum. Longer lengths can be used if it is desirable to have the sleeve empty in the distal jejunum or ileum. In certain embodiments, the sleeve 400 may be configured with a length of 100 cm as this is a standard length of the roux limb in a Roux-en-Y gastric bypass. A sleeve 400 with a length of approximately 500 cm or more can be used to perform a nonsurgical biliopancreatic diversion for achieving results similar to a Scopinaro procedure. In one configuration, the gastrointestinal sleeve device 400 has an approximately constant diameter of approximately 0.75-2.5 cm through the duodenum portion 416 and the jejunum portion 418. This diameter is less than the internal diameter of the small intestine through these sections to allow free flow of gastric, biliary, pancreatic and intestinal secretions along the outside of the sleeve. This diameter can be optimized for individual patients where a smaller diameter may be tolerated better and a larger diameter may be superior regarding the passage of food. Collapsibility may allow use of larger diameter sleeves, while sleeves of smaller diameter and greater resilience may be clinically indicated to minimize irritation.

Past the pylorus and past the duodenum, the gastrointestinal sleeve device 400 may include means to couple peristaltic muscular action of the intestine and use it to apply antegrade tension to the sleeve. One or more rings 420 in the sleeve may provide this coupling. The rings 420 may include a metallic spring to return the ring to its circular shape if collapsed by either the installation procedure or by peristaltic action of the intestine. The rings 420 may be positioned in the jejunum, as the duodenum exhibits little or no peristalsis. Alternatively, the exterior of the sleeve may be configured with small bumps or other features to provide a small amount of friction for coupling with the peristaltic muscular action of the intestine. A balance can be struck between friction and lubricity on the exterior of the sleeve. There should be enough friction so that peristalsis will act to straighten the sleeve and apply a small amount of tension to keep it in place. Too much friction, however, will allow the intestinal wall to "climb" up the exterior of the sleeve due to peristalsis, which would generally not be desirable. For example, this balance can be achieved using a smooth polyurethane sleeve with PHOTO-LINK LUBRICIO COATING (Surmodics Inc.) or other lubricious coatings. However, in some clinical situations it may be desirable to achieve this end result. This can be achieved by using rings or other means of mechanically coupling the sleeve with the intestinal peristaltic action. In this case the intestine essentially crawls up the sleeve and takes on a pleated bellows-like configuration. This can have the result of effectively lengthening the sleeve, as food would now exit the sleeve at a more distal location within the intestine.

It may be desirable in some clinical circumstances to provide a temporary peristalsis coupling that can straighten the sleeve for a period of time after insertion and not couple with the peristaltic action after this period. This will tend to reduce the climbing of the intestine and can allow any previous change in the position of the intestine to return to normal. This can be accomplished by using a biodegradable coupling means such as a dissolvable peristalsis ring or a high friction coating that comes off, leaving a lubricious surface. A balloon that detaches or deflates could be another means of accomplishing this end. For example, the balloons and other features in FIGS. 18A, 18B and 18C can be configured for this application. Such balloons can be made self-deflating by the inclusion of a dissolvable portion or by inflation with a hypoosmolar fluid combined with use of osmotically active balloon membrane. In this event the inflation fluid will escape the balloon through the membrane due to the osmotic imbalance between the inflation fluid and the contents of the intestine.

Optionally, the gastrointestinal sleeve device 400, along some or all of its length, may be configured by means of controlled wall thickness or reinforcing so that, if the sleeve is folded or kinked, open channels 442 will be maintained, as shown in FIGS. 12A, 12B and 12C. In this case locally increased wall rigidity may also be used to control the fold preferences of the sleeve.

Alternatively, the gastrointestinal sleeve device 400, along some or all of its length, may include axial channels 444, as shown in FIGS. 13A and 13B. The axial channels would be configured so that, in the event of a fold or kink in the sleeve, the lumen of the sleeve remains patent and open. These channels can also be formed by peaks and valleys in a constant thickness sleeve wall in addition to the manner diagrammed.

In one embodiment of the gastrointestinal sleeve device 400, the gastric and intestinal portions of the sleeve are constructed to be normally collapsed to a somewhat flattened configuration when in a rest position, such as is shown in FIG. 12B, 12C or 13B. This can minimize the potential for irritation of the mucosa in the stomach, the pylorus and the intestine and other structures such as the ampula of Veder. The sleeve may open or expand to a circular cross section, as shown in FIG. 12A or 13A, for the passage of ingested food. Thus the stomach and intestinal walls would not be constantly subjected to stimulation, which could result in increased secretion and/or peristaltic action. Alternatively, some or all of the gastric and intestinal portions of the sleeve may be constructed to remain in an open or expanded configuration when in a rest position and to easily collapse when subjected to external pressure, for example to allow passage of digestive secretions along the exterior or the sleeve. This second option may also include diametric sizing based upon the clinical desirability of stimulating the passage wall (similar diameter to passage) or not (smaller diameter than passage).

The gastrointestinal sleeve device 400 is generally impermeable along its entire length to isolate ingested food from digestive secretions. However, it may be desirable to have the gastrointestinal sleeve device 400 having semipermeable or controlled permeability properties along some or all of its length to allow absorption of certain nutrients at the appropriate location in the stomach or intestine in order to avoid malabsorption complications while still limiting caloric absorption. For example, in the duodenal portion it would be beneficial to allow Iron and B-12 to exit the sleeve so that it can be absorbed through the intestinal wall.

FIG. 14 illustrates an optional one-way valve 450 feature of the gastrointestinal sleeve device. Positioning of valves may be patient dependent. One clinically significant location could be at or near the transition from the duodenum, where there is little or no peristaltic action and the jejunum where peristalsis occurs. Other significant locations include the distal opening of the device (to prevent flow into the sleeve), the proximal opening of the device (to prevent reflux into the esophagus) and at or near the pylorus (to help ingested food pass through the pylorus and duodenum). A valve upstream of a restriction may also help, in combination with contractions or peristalsis of the stomach, to force ingested food through the restriction.

Figure 15:
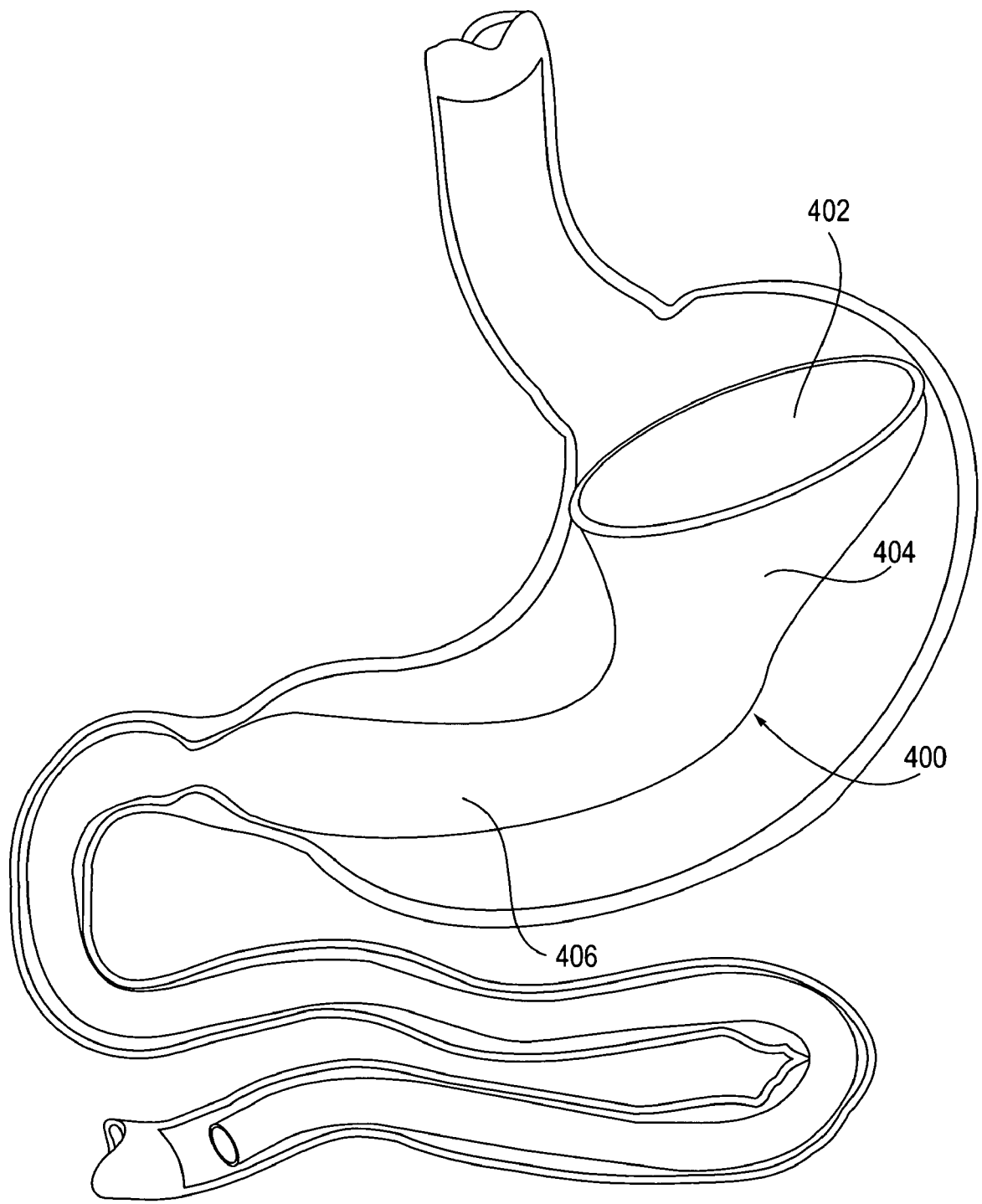
FIG. 15 illustrates another example of a gastrointestinal sleeve device deployed within a patient's gastrointestinal tract for treating morbid obesity.

FIG. 15 illustrates another example of a gastrointestinal sleeve device 400 deployed within a patient's gastrointestinal tract for treating morbid obesity. In this embodiment, the proximal opening 402 of the gastrointestinal sleeve device 400 has a flared opening that is configured for attachment at the cardiofundal border. Attachment at the cardiofundal border confers different advantages to the gastrointestinal sleeve device 400, as described above. Attachment can be made using any of the methods described herein. The proximal opening 402 has a diameter of approximately 2-10 cm, which smoothly tapers down to a diameter of approximately 1.5-4.0 cm through the fundus portion 404 and the antrum portion 406 of the sleeve. The remainder of the gastrointestinal sleeve device 400 may be configured similarly to the embodiment described in connection with FIG. 8.

Figure 16:
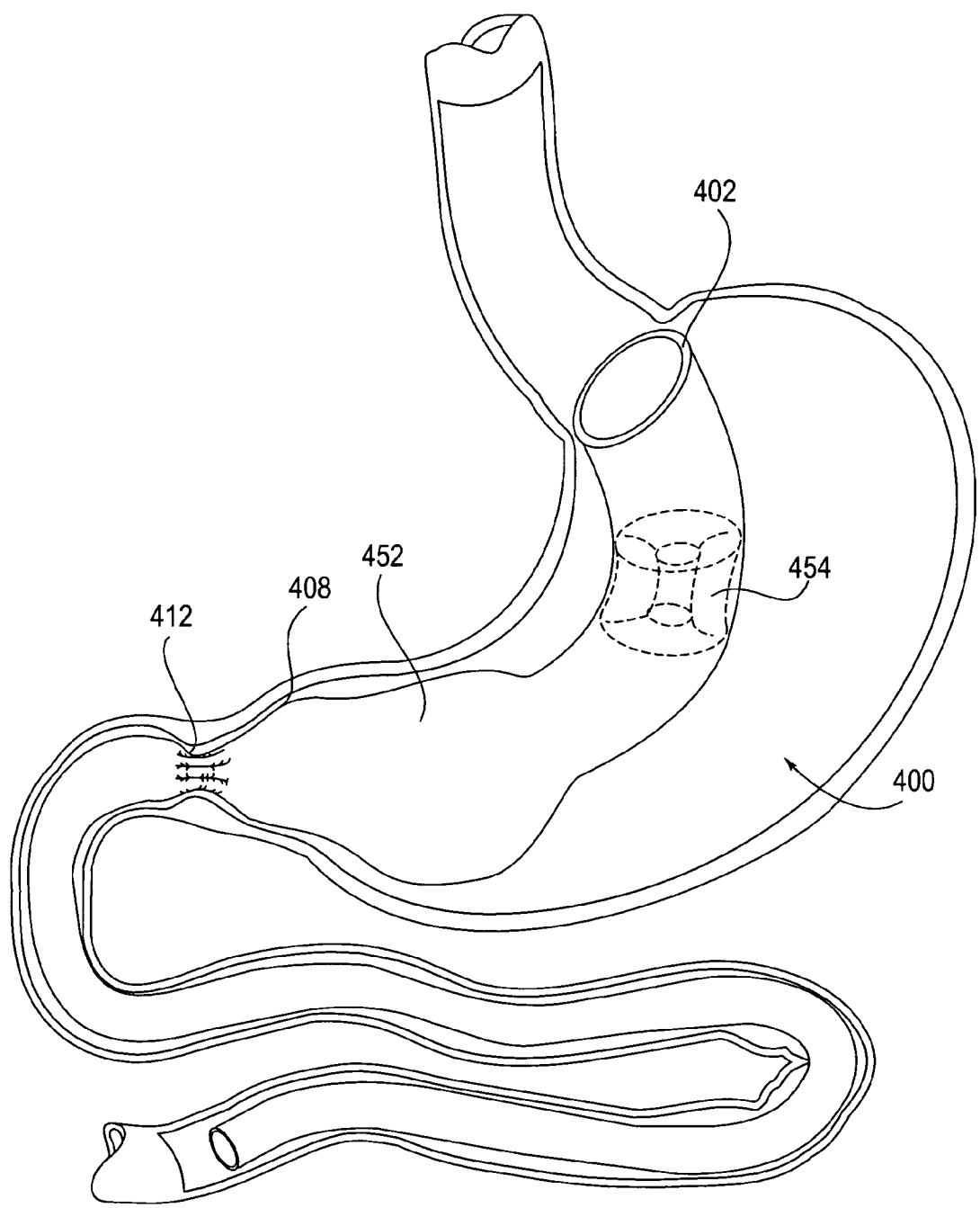
FIG. 16 illustrates another example of a gastrointestinal sleeve device having a reservoir located above the patient's pyloric sphincter.

FIG. 16 illustrates another example of a gastrointestinal sleeve device 400 having a reservoir 452 located above the patient's pyloric sphincter. The reservoir 452 allows ingested food to accumulate in the antrum of the stomach and to apply pressure against the pylorus, which may contribute to periodic opening of the pyloric sphincter for proper emptying of the stomach contents. Alternatively or in addition, a reservoir 452 may be positioned elsewhere in the gastrointestinal system, for example just below the GEJ, to provide a sensation of fullness and satiety. FIG. 16 also illustrates the optional feature of a restriction 454 in the gastrointestinal sleeve device 400 between the proximal opening 402 and the upstream end 408 of the pylorus. The restriction 454 can be provided by a simple narrowing of the sleeve 400 or, as illustrated in this embodiment, can be provided by a stoma device 454 positioned within the lumen of the sleeve 400. The stoma device 454 can be an adjustable stoma device, a smart stoma or any of the stoma devices described herein. Positioning of the stoma device relative to the proximal sleeve opening can be selected as clinically indicated to provide a reservoir for food proximal to a restriction that is appropriate for the desired weight loss. In other embodiments of the gastrointestinal sleeve device 400, sufficient reduced volume or resistance to ingestion of food for encouraging weight loss may be provided by the length and diameter of the gastric portion of the sleeve 400 without the need for a stoma device or other restriction other than the use of the pylorus as a natural restriction as described above.

When the pylorus is used as a natural stoma to control food flow, an electrical stimulation system can optionally be used to control the opening and closing of the pylorus. This system could include one or more electrodes for stimulating the pylorus, a stimulator (including power source and controlling electronics) and one or more optional sensing electrodes.

Figure 17:
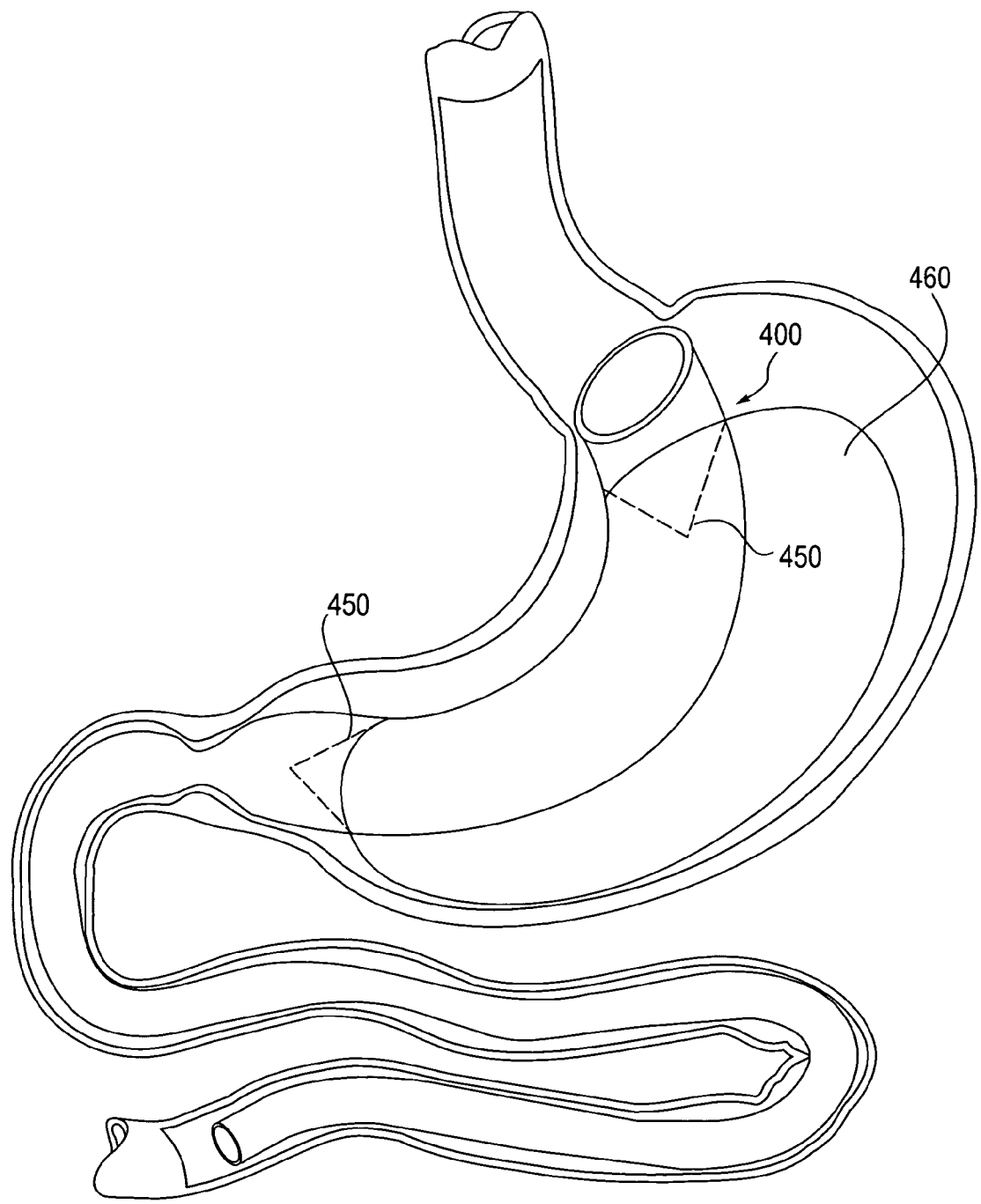
FIG. 17 illustrates another example of a gastrointestinal sleeve device having an inflatable gastric balloon.

FIG. 17 illustrates another example of a gastrointestinal sleeve device 400 having an inflatable gastric balloon 460 to enhance satiation by taking up volume in the stomach. The gastric balloon 460 may be arranged coaxially around the sleeve or it may be configured to inflate preferentially toward the greater curvature of the stomach, as shown in FIG. 17. The gastric balloon 460 may be inflated within the patient's stomach using a detachable tether and a self-sealing valve. Alternatively, the gastric balloon 460 may be made self-inflating by having a hyperosmolar material within the gastric balloon 460 and an osmotically active balloon membrane (complete or partial). The gastric balloon 460 can be configured to transmit peristaltic motion to the interior of the gastrointestinal sleeve device 400 to help ingested food transit through the sleeve as described above. Optionally, the sleeve under and around the gastric balloon 460 may be combined with one or more one-way valves 450 positioned upstream and/or downstream of the gastric balloon to assist peristaltic action to urge ingested food through the sleeve.

Figure 18A:
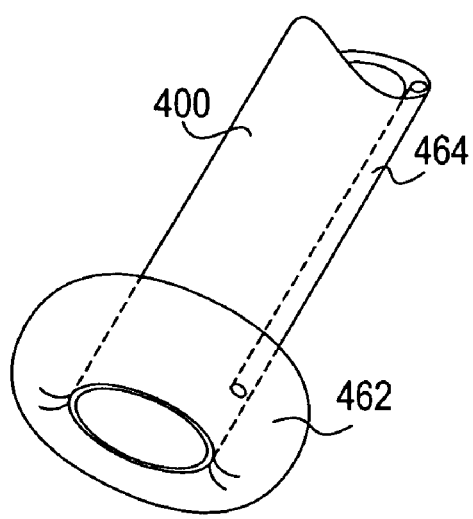
FIGS. 18A-18D illustrate optional features to assist in the deployment of the gastrointestinal sleeve device within a patient's gastrointestinal tract.

FIGS. 18A, 18B, 18C and 18D illustrate optional features to assist in the deployment of the gastrointestinal sleeve device within a patient's gastrointestinal tract. FIG. 18A illustrates a gastrointestinal sleeve device 400 having an inflatable balloon 462 on its distal end. The balloon 462 is inflated via an inflation lumen 464 that extends through the gastrointestinal sleeve device 400. The inflation lumen 464 can be incorporated into the wall of sleeve 400 or it can be in a coaxial tubular tether that can be separated from the sleeve 400 to deflate the balloon 462 once the sleeve is fully deployed within the patient's intestine. The balloon 462 is inflated after the distal end of the sleeve 400 is past the pylorus and the inflated balloon is carried distally by peristaltic action of the intestines. Once the sleeve is fully deployed within the patient's intestine, the balloon 462 can be deflated. The balloon can alternately be inflated prior to insertion into the body, thereby not requiring an inflation lumen the length of the device, and can either deflate naturally or have an active means of deflation as described herein. In an alternate embodiment the means to attach the balloon to the distal sleeve would be biodegradable and after the degradation of the attachment means the balloon would pass through the digestive tract naturally.

Figure 18B:
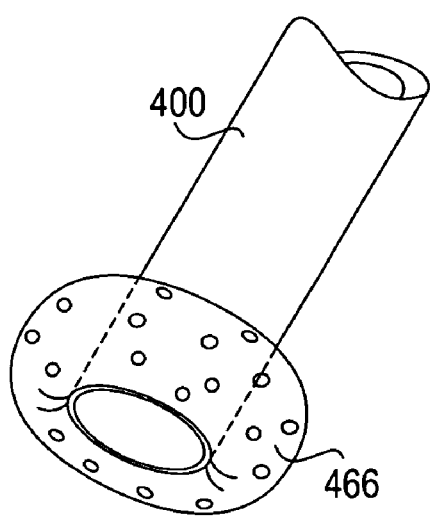

FIG. 18B illustrates a gastrointestinal sleeve device 400 having a sponge or foam member 466 on its distal end. The use of a foam member 466 simplifies the gastrointestinal sleeve device 400 in that an inflation lumen is unnecessary to expand the foam member 466. The foam member 466 is allowed to expand after the distal end of the sleeve 400 is past the pylorus and the expanded foam member 466 is carried distally by peristaltic action of the intestines. The foam member 466 can be biodegradably attached, as described above, or made of a dissolvable or digestible material so that it disappears after it has served its purpose.

Figure 18C:
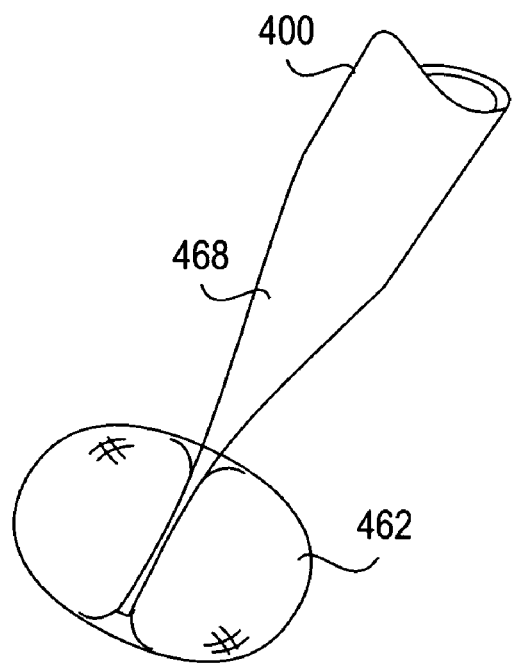

FIG. 18C illustrates a variation of the gastrointestinal sleeve device 400 of FIG. 18A, wherein the inflatable balloon 462 is mounted on a flexible tail 468 formed on or attached to the distal end of the sleeve.

Figure 18D:
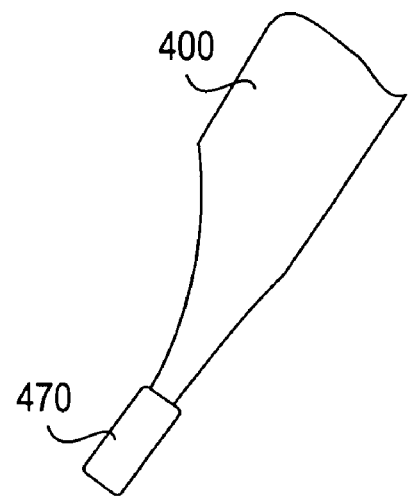

FIG. 18D illustrates a variation of the gastrointestinal sleeve device 400 of FIG. 18C, wherein the inflatable balloon is replaced with a magnet 470. This magnet 470 can be used in conjunction with other magnets, to guide the deployment of the intestinal sleeve. Matching guide magnets of opposing polarity can be used internal to the intestine in conjunction with an endoscope, within the abdomen external to the intestine in conjunction with a laparoscope or external to the body in a manner similar to that described by Gabriel in U.S. Pat. No. 5,431,640. In an alternate embodiment the means to attach the magnet to the distal sleeve would be biodegradable and after the degradation of the attachment the magnet would pass through the digestive tract naturally.

In summary, the present invention provides a gastrointestinal sleeve device which allows separation of ingested foods and liquids from digestive secretions through the stomach and past the duodenum and optionally into the jejunum or ileum. This is of particular significance because gastric acids are neutralized by bile and duodenal secretions. This prevents digestion from gastric acid taking place even if the food and gastric secretions are allowed to mix at a later point in the intestines.

Figure 19:
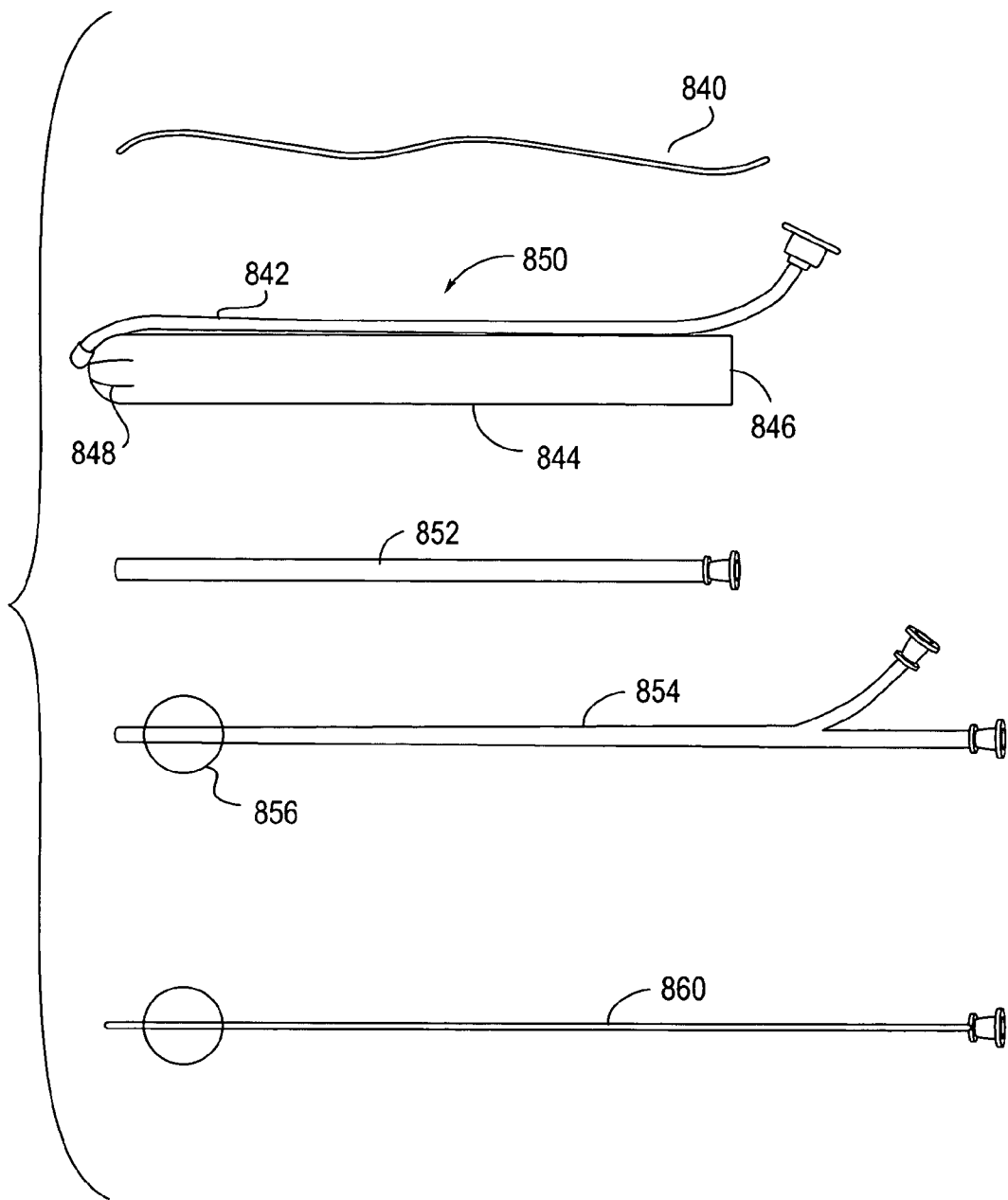
FIG. 19 illustrates the components of a kit for delivering and deploying a gastrointestinal sleeve device.

FIG. 19 illustrates the components of a kit for delivering and deploying a gastrointestinal sleeve device. In one embodiment, the kit includes an optional guidewire 840, a pyloric/duodenal introducer 850, and either a distal pusher catheter 852 or a distal balloon seal 856 and pusher catheter 854. A balloon catheter 860 for removal of the gastrointestinal sleeve device may be included as part of the kit or supplied as a separate item. For example this balloon catheter can be used for retrieval as described in step 12 of the method outlined below. As an alternative to the use of a balloon catheter for retrieval, an endoscopic grasper such as those in the MAXUM line (Wilson-Cook) can be passed coaxially down the sleeve or delivered externally to the sleeve through the working channel of an endoscope then clamped onto the sleeve at some distal location and then used to retract the distal sleeve.

The pyloric/duodenal introducer 850 has a tubular body 844 with an introducer lumen 846 sized to pass through the gastrointestinal sleeve device. The tubular body 844 has a length sufficient to reach past the patient's pylorus into the duodenum via a peroral route. In certain embodiments, the tubular body 844 has a slit flowering distal end 848 for atraumatic crossing of the pylorus. An optional distal infusion lumen 842 parallels the introducer lumen 846 and allows infusion of fluids near the distal end of the introducer 850. For example, the introducer can be used as described in step 10g of the method outlined below.

Figure 20A:
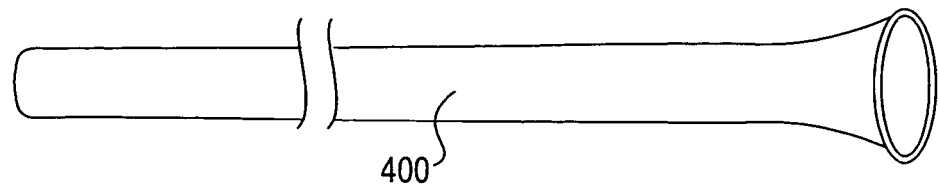
FIGS. 20A-20C illustrate three options for preloading a gastrointestinal sleeve device for delivery and deployment.
Figure 20B:
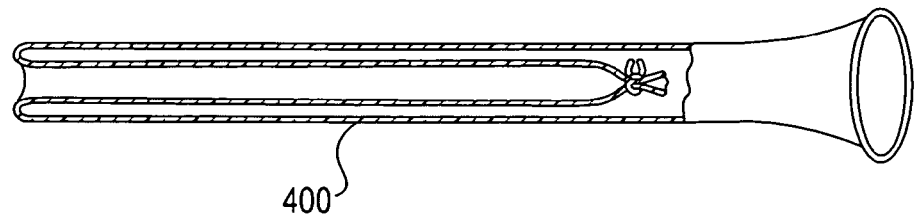
Figure 20C:
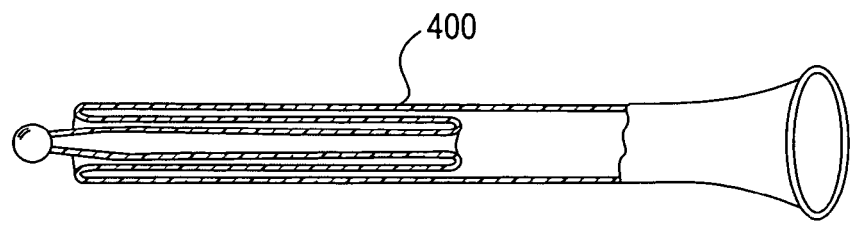

FIGS. 20A-20C illustrate three options for preloading a gastrointestinal sleeve device 400 for delivery and deployment. FIG. 20A shows a gastrointestinal sleeve device 400 in a straight configuration. This configuration is the simplest for construction and loading of the gastrointestinal sleeve device 400, however it poses some challenges for delivery and deployment within the patient's gastrointestinal system. The straight gastrointestinal sleeve device 400 would have to be inserted full-length into the patient's small intestines, which would be challenging because of the torturous path of the small intestines. Another strategy is to invert the gastrointestinal sleeve device 400 so that it would only have to be directly inserted past the patient's pylorus, with peristaltic action assisting the deployment of the device within the patient's small intestines by eversion of the inverted sections. FIG. 20B shows a gastrointestinal sleeve device 400 loaded in a fully inverted configuration. FIG. 20C shows a gastrointestinal sleeve device 400 loaded in a double-inverted configuration. This simplifies the delivery and deployment of the device, but it adds some additional constraints to the configuration of the device. The inverting segments can have very thin walls and inverting interfaces can be highly lubricious for easy and reliable deployment. For example blow molded 90A durometer polyurethane of a wall thickness on the order of 0.005" or less, most preferably about 0.002", with a lubricious coating will work in this manner. The double inverted configuration has the advantage of having the option to use a distal balloon, or other structure as described earlier, to assist the peristalsis working on its distal end to evert the sleeve. This may avoid the need to use internal pressure to accomplish the eversion.

Figure 21A:
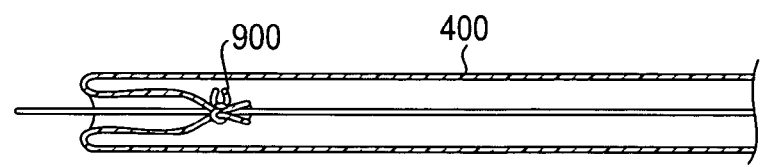
FIGS. 21A-21D illustrate four options for sealing the distal end of a gastrointestinal sleeve device during delivery and deployment.
Figure 21B:
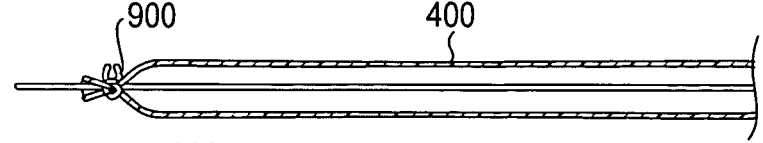
Figure 21C:
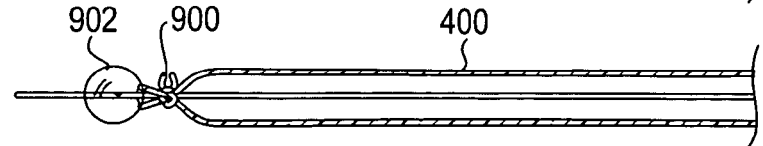
Figure 21D:
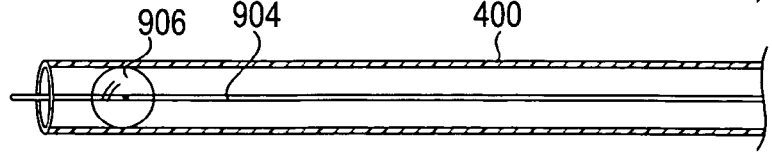

The gastrointestinal sleeve device 400 in FIGS. 20B and 20C could be optionally everted using the method of internal pressurization that is well known in the everting catheter art. To maintain the internal fluid pressure used to assist in everting the inverted gastrointestinal sleeve device 400, the distal end of the device may be temporarily sealed during deployment. FIGS. 21A-21D illustrate four options for sealing the distal end of a gastrointestinal sleeve device during delivery and deployment. FIG. 21A shows the inverted distal end of the gastrointestinal sleeve device 400 sealed with a biodegradable tie 900 that is formulated to dissolve within approximately 24 hours in the intestines. Dissolution of the biodegradable tie 900 can be aided by a solvent or active agent that is ingested or placed in the optional everting fluid. FIG. 21B shows the noninverted distal end of the gastrointestinal sleeve device 400 sealed with a biodegradable tie 900 that is formulated to dissolve within approximately 24 hours in the intestines. FIG. 21C shows an inflatable balloon 902 that extends past the distal end of the gastrointestinal sleeve device 400. The gastrointestinal sleeve device 400 can be attached and/or sealed with a biodegradable tie 900 proximal to the balloon 902. The balloon 902 is carried along through the intestine by peristalsis to deploy the gastrointestinal sleeve device 400 by eversion of the inverted section. When the biodegradable tie 900 dissolves, the balloon 902 detaches and deflates and is carried harmlessly out through the intestines. The inflatable balloon 902 may also be made of a biodegradable material. FIG. 21D shows a balloon catheter 904 with an inflatable balloon 906 that is inflated within the gastrointestinal sleeve device 400 to form a seal. Once the gastrointestinal sleeve device 400 is fully deployed, the balloon 906 is deflated and the balloon catheter 904 is withdrawn. Please note that the aforementioned 24 hour dissolution time is an example and, depending on the clinical situation, this time period could range from a few hours to many weeks.

Figure 22A:
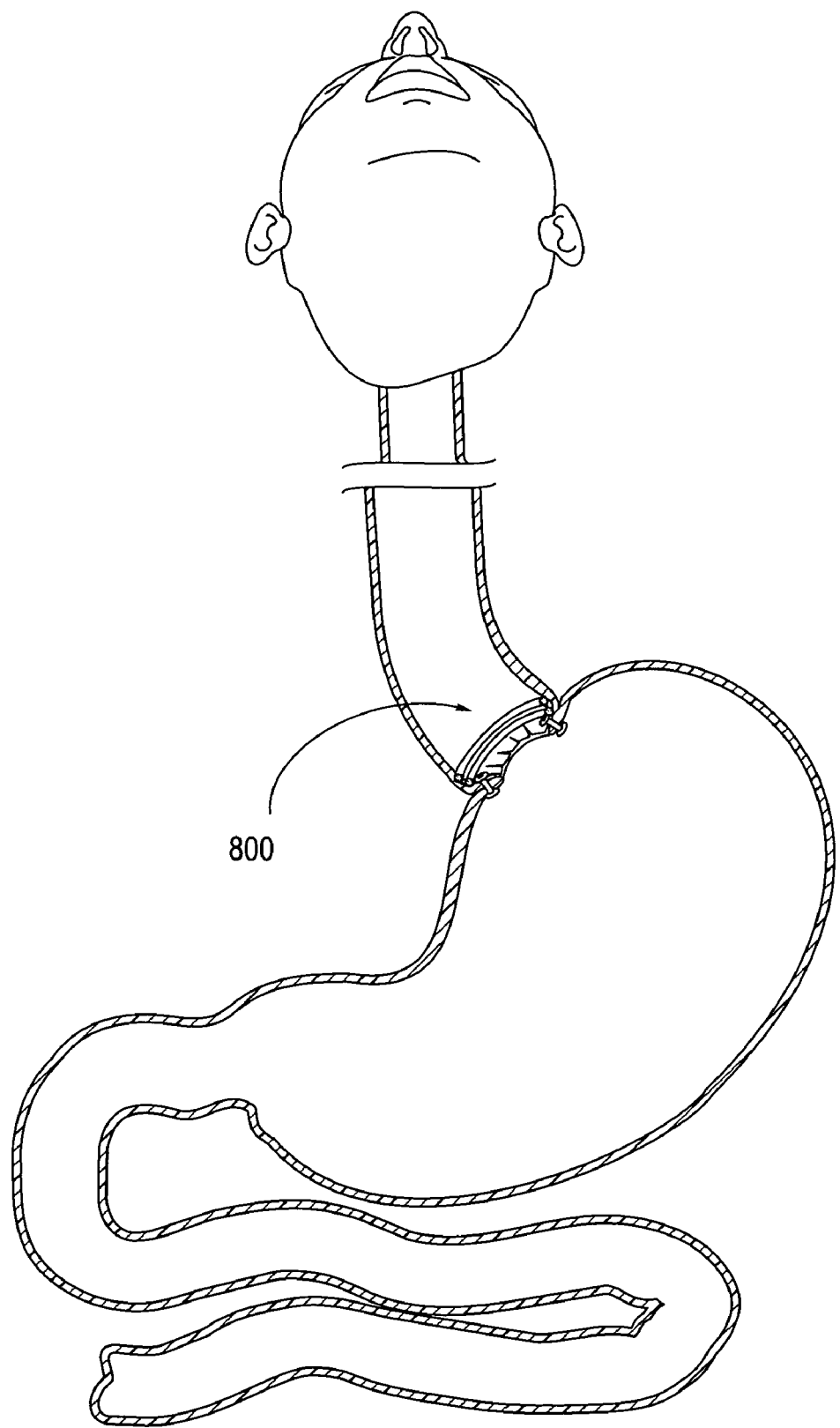
FIGS. 22A-22B illustrate a method of delivering and deploying a gastrointestinal sleeve device.
Figure 22B:
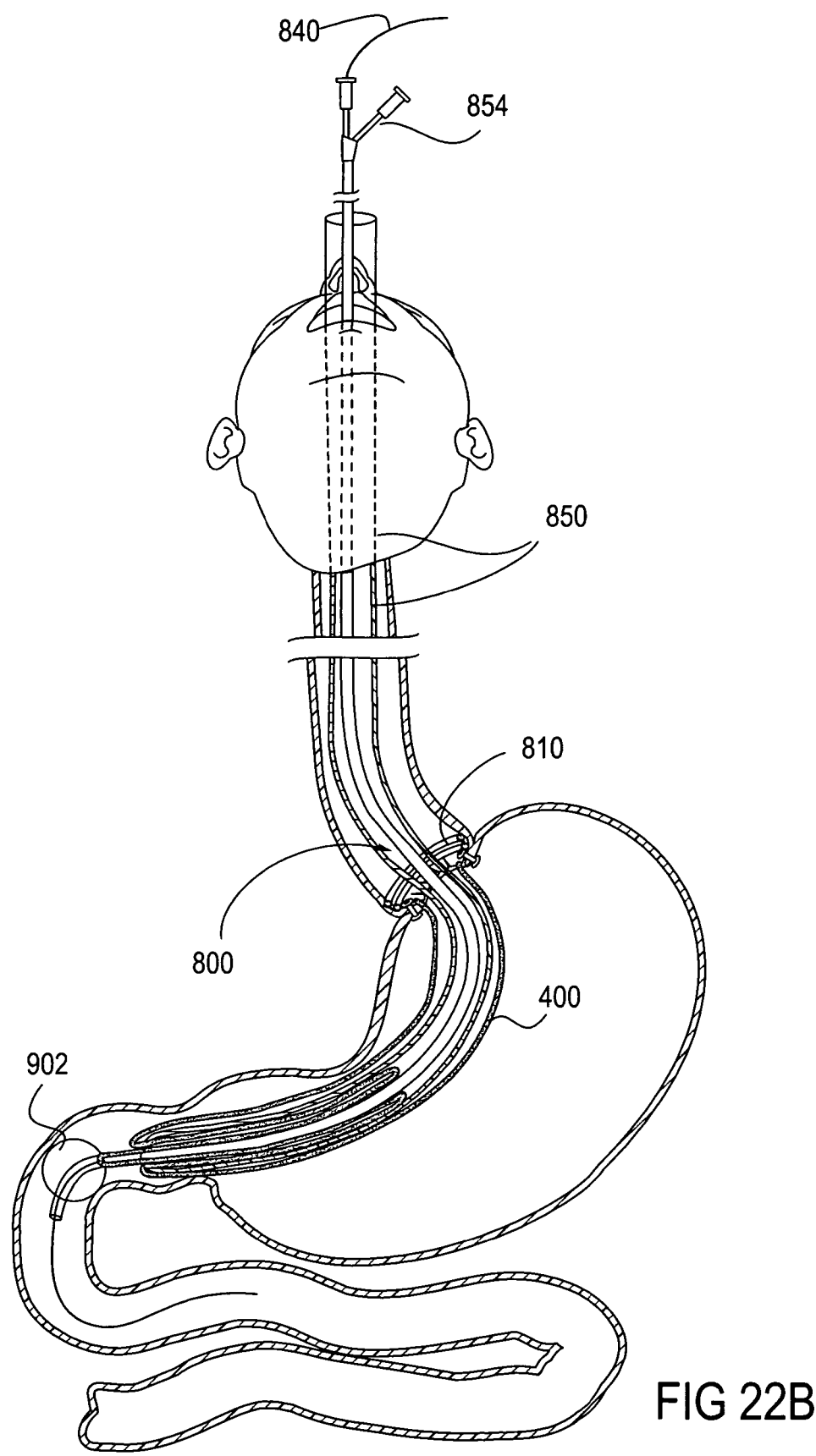

FIGS. 22A-22B illustrate a method of delivering and deploying a gastrointestinal sleeve device 400. First, an attachment ring device 800 or the like is installed in the patient's stomach using any of the devices and methods previously describe, as shown in FIG. 22A. Subsequently, the pyloric/duodenal introducer 850 with the gastrointestinal sleeve device 400 loaded into it is inserted through the patient's pylorus via a peroral route, as shown in FIG. 22B. In this example, the proximal portion of the gastrointestinal sleeve device 400 is external to the pyloric/duodenal introducer 850 and the distal portion of the sleeve is double inverted inside of the introducer 850 similar to the sleeve shown in FIG. 21C. The sleeve ring 810 is installed in the attachment ring device 800 and the pyloric/duodenal introducer 850 is withdrawn. Then, using a combination of fluid pressure, a push rod or catheter 854 inside of the gastrointestinal sleeve device 400 and/or peristalsis of the intestines, optionally assisted by an inflatable balloon on the catheter or a biodegradably attached distal peristalsis balloon 902, the gastrointestinal sleeve device 400 everts to a fully deployed position.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A method of treating a patient, comprising the steps of:
providing a gastrointestinal sleeve device having an elongate tubular body, with a proximal end and a distal end;
positioning the gastrointestinal sleeve device in the patient's digestive tract such that the proximal end of the tubular body is positioned at the native gastroesophageal junction to receive ingested food and liquids from the patient's esophagus and the distal end of the tubular body is positioned in the patient's jejunum, and
attaching the proximal end of the tubular body to the patient at the native gastroesophageal junction.

2. A method of treating a patient as in claim 1, wherein the attaching step comprises using a suture.

3. A method of treating a patient as in claim 1, wherein the attaching step comprises suturing the tubular body to the wall of the digestive tract at the native gastroesophageal junction.

4. A method of treating a patient as in claim 1, wherein at least a portion of a wall of the tubular body is porous.

5. A method of treating a patient as in claim 1, wherein the tubular body is impermeable such that the tubular body acts as a partial internal intestinal bypass.

6. A method of treating a patient as in claim 1, wherein the providing step comprises providing the tubular body with a funnel opening on the proximal end.

7. A method of treating a patient, comprising the steps of:
providing a gastrointestinal sleeve device having an elongate tubular body, with a proximal end having a funnel opening and a distal end, wherein at least a portion of a wall of the tubular body is porous; and
positioning the gastrointestinal sleeve device in the patient's digestive tract such that the proximal end of the tubular body is positioned at the native gastroesophageal junction to receive ingested food and liquids from the patient's esophagus and the distal end of the tubular body is positioned in the patient's jejunum.

8. A method of treating a patient as in claim 7, further comprising the step of attaching the proximal end of the tubular body to the patient at the native gastroesophageal junction.

9. A method of treating a patient as in claim 7, wherein the attaching step comprises using a suture.

10. A method of treating a patient as in claim 7, wherein the attaching step comprises suturing the tubular body to the wall of the digestive tract at the native gastroesophageal junction.

* * * * *

UNITED STATES PATENT AND TRADEMARK OFFICE
CERTIFICATE OF CORRECTION

PATENT NO. : 7,794,447 B2  
APPLICATION NO. : 10/903255  
DATED : September 14, 2010  
INVENTOR(S) : Dann et al.

It is certified that error appears in the above-identified patent and that said Letters Patent is hereby corrected as shown below:

On the Title Page, Item (63) under "Related U.S. Application Data" after "Continuation of Application No. 10/698,148, filed on Oct. 31, 2003", please add --Provisional application No. 60/422,987, filed on Nov. 1, 2002. Provisional application No. 60/430,857, filed on Dec. 3, 2002. Provisional application No. 60/437,513, filed on Dec. 30, 2002. Provisional application No. 60/448,817, filed on Feb. 21, 2003. Provisional application No. 60/480,485, filed on Jun. 21, 2003--.

On Title page 3, Item (56) 2nd col. line 36, please delete "Prelinary" and insert --Preliminary--.

On Title page 4, Item (56) 2nd col. line 10, please delete "Gastrointestial" and insert --Gastrointestinal--.

At column 8, lines 14-15, please delete "LUBRICIO" and insert --LUBRICIOUS--.

At column 13, line 42, please delete "polyglecaprone" and insert --poliglecaprone--.

At column 13, line 43, please delete "Vycril" and insert --Vicryl--.

At column 28, line 65, please delete "LUBRICIO" and insert --LUBRICIOUS--.

At column 24, line 50, please delete "claim 7," and insert --claim 8--.

At column 24, line 52, please delete "claim 7" and insert --claim 9--.

Signed and Sealed this  
Thirteenth Day of March, 2012

David J. Kappos  
*Director of the United States Patent and Trademark Office*